US010100078B2

(12) United States Patent
Morein et al.

(10) Patent No.: US 10,100,078 B2
(45) Date of Patent: Oct. 16, 2018

(54) NANOPARTICLES, PROCESS FOR PREPARATION AND USE THEREOF AS CARRIER FOR AMPHIPATIC AND HYDROPHOBIC MOLECULES IN FIELDS OF MEDICINE INCLUDING CANCER TREATMENT AND FOOD RELATED COMPOUNDS

(71) Applicant: MX Adjuvac AB, Enkoping (SE)

(72) Inventors: Bror Morein, Uppsala (SE); Saideh Berenjian, Uppsala (SE); Kafei Hu, Uppsala (SE)

(73) Assignee: MX Adjuvac AB, Enkoping (SE)

( * ) Notice: Subject to any disclaimer, the term of this patent is extended or adjusted under 35 U.S.C. 154(b) by 0 days.

(21) Appl. No.: 15/605,595

(22) Filed: May 25, 2017

(65) Prior Publication Data
US 2017/0260224 A1   Sep. 14, 2017

Related U.S. Application Data

(62) Division of application No. 14/349,142, filed as application No. PCT/SE2012/051048 on Oct. 1, 2012.

(60) Provisional application No. 61/542,425, filed on Oct. 3, 2011.

(51) Int. Cl.
| *G01N 33/536* | (2006.01) |
| *C07J 9/00* | (2006.01) |
| *A61K 31/255* | (2006.01) |
| *A61K 31/337* | (2006.01) |
| *A61K 31/52* | (2006.01) |
| *A61K 31/593* | (2006.01) |
| *A61K 31/704* | (2006.01) |
| *A61K 31/7068* | (2006.01) |
| *A61K 39/145* | (2006.01) |
| *A61K 39/39* | (2006.01) |
| *A61K 36/73* | (2006.01) |
| *C12Q 1/48* | (2006.01) |
| *G01N 33/50* | (2006.01) |
| *A61K 9/51* | (2006.01) |
| *A61K 39/12* | (2006.01) |
| *A61K 39/00* | (2006.01) |

(52) U.S. Cl.
CPC ............... *C07J 9/00* (2013.01); *A61K 9/5123* (2013.01); *A61K 31/255* (2013.01); *A61K 31/337* (2013.01); *A61K 31/52* (2013.01); *A61K 31/593* (2013.01); *A61K 31/704* (2013.01); *A61K 31/7068* (2013.01); *A61K 36/73* (2013.01); *A61K 39/12* (2013.01); *A61K 39/145* (2013.01); *A61K 39/39* (2013.01); *C12Q 1/485* (2013.01); *G01N 33/5011* (2013.01); *A61K 2039/5252* (2013.01); *A61K 2039/55555* (2013.01); *A61K 2039/55577* (2013.01); *C12N 2760/16134* (2013.01); *C12N 2760/16234* (2013.01); *G01N 2800/52* (2013.01); *Y10T 428/2982* (2015.01)

(58) Field of Classification Search
CPC ........................................................ C07J 9/00
See application file for complete search history.

(56) References Cited

U.S. PATENT DOCUMENTS

| 4,900,549 | A | 2/1990 | De Vries |
| 5,620,690 | A | 4/1997 | Kersten et al. |
| 5,650,398 | A | 7/1997 | Kensil et al. |
| 5,679,354 | A | 10/1997 | Morein et al. |
| 6,316,030 | B1 | 11/2001 | Kropf et al. |
| 6,352,697 | B1 | 3/2002 | Cox et al. |
| 6,506,386 | B1 | 1/2003 | Friede et al. |
| 6,861,410 | B1 | 3/2005 | Ott et al. |
| 8,889,146 | B2 | 11/2014 | Vassilev et al. |
| 2001/0053365 | A1 | 12/2001 | Friede et al. |
| 2003/0017197 | A1 | 1/2003 | Shorr et al. |
| 2003/0118635 | A1 | 6/2003 | Dalsgaard |
| 2003/0180244 | A1 | 9/2003 | Soane |
| 2005/0175623 | A1 | 8/2005 | Wang |
| 2008/0194494 | A1 | 8/2008 | Martinez et al. |
| 2008/0243049 | A1 | 10/2008 | Hardy |
| 2008/0292686 | A1 | 11/2008 | Garcon |
| 2009/0156692 | A1 | 6/2009 | Soane |
| 2009/0324641 | A1 | 12/2009 | Dominowski et al. |

(Continued)

FOREIGN PATENT DOCUMENTS

| CA | 2064911 A1 | 8/1990 |
| WO | 9221331 | 12/1992 |

(Continued)

OTHER PUBLICATIONS

Bankefors, "Methods for Structural Characterisation of Quillaja Saponins by Electrospray Ionisation Ion Trap Multiple-Stage Mass Spectrometry," Doctoral Thesis, Swedish University of Agricultural Sciences, Uppsala, 2008.
Baxter, M.K., et al., "An Acidic Amphipathic Helix in the Bovine Papilomavirus E2 protein is Critical for DNA Replication and Interation with the E1 Protein" Virology, 2005, 332:78-88.
Copland, M. et al., "Hydration of lipid films with an aqueous solution of Quil A: a simple method for the preparation of immune-stimulating complexes", International Journal of Pharmaceutics, 2000, 196:135-139.
Fleck, J. et al., "Adjuvant activity of quillaja brasillinesis saponins on the immune responses to bovine herpesvirus type 1 in mice" Vaccine, 2006, 7129-7134.

(Continued)

*Primary Examiner* — Albert M Navarro
(74) *Attorney, Agent, or Firm* — Andrus Intellectual Property Law, LLP

(57) ABSTRACT

The present invention regards nanoparticles comprising a sterol and a component derived from *Quillaja saponaria* Molina selected from quillaja acid and *quillaja* saponin, which nanoparticles do not comprise a phospholipid. It also relates to a composition comprising the nanoparticles, and the use thereof as adjuvant, especially in vaccines, as carriers for amphipathic or hydrophobic molecules and as agents for treatment of cancer. Further, it regards a method for producing the phospholipid-free nano particles, a method for the treatment of cancer and a method for assessing the applicability of the cancer treating method.

8 Claims, 9 Drawing Sheets

(56) References Cited

U.S. PATENT DOCUMENTS

Figure 1:
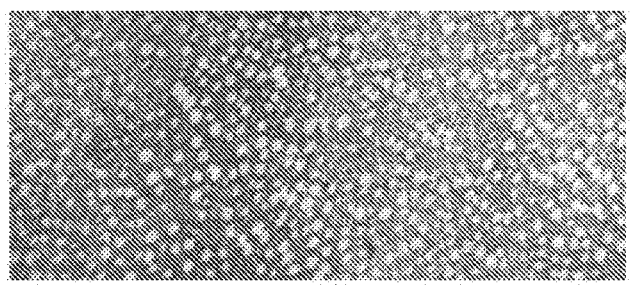

| | | |
|---|---|---|
| 2010/0035307 A1 | 2/2010 | Zelder et al. |
| 2010/0150994 A1 | 6/2010 | Kotyla |
| 2010/0221345 A1 | 9/2010 | Akiyoshi et al. |
| 2010/0291146 A1 | 11/2010 | Pearse et al. |
| 2011/0053365 A1 | 3/2011 | Hwang et al. |
| 2011/0206729 A1 | 8/2011 | Akiyoshi et al. |
| 2012/0093847 A1 | 4/2012 | Baudoux et al. |
| 2013/0236533 A1 | 9/2013 | Von Adrian et al. |
| 2013/0302369 A1 | 11/2013 | Abdelmagid et al. |
| 2014/0199233 A1 | 7/2014 | Nagy et al. |
| 2014/0322271 A1 | 10/2014 | Garcon-Johnson et al. |

FOREIGN PATENT DOCUMENTS

| | | |
|---|---|---|
| WO | 9912565 A2 | 3/1999 |
| WO | 02080981 | 10/2002 |
| WO | 2004004762 | 1/2004 |
| WO | 2005002620 | 1/2005 |
| WO | 2009156960 | 12/2009 |
| WO | 2010023216 | 3/2010 |
| WO | 2013051994 | 4/2013 |

OTHER PUBLICATIONS

Kersten, G.F.A. et al., "On the structure of immune-stimulating saponin-lipid complexes (iscoms)", Biochimica et Biophysica Aca, 1062 (1991) 165-171.
Mitra et al., "Cholesterol Solubilization in Aqueous Micellar Solutions of Quillaja Saponin, Bile Salts, or Nonionic Surfactants", J. Agric. Food Chem., 2001, 49:384-394.
International Search Report for PCT/SE2012/051048, dated Jan. 30, 2013.
International Search Report for PCT/SE2014/050380 dated Jul. 17, 2014.
Office Action for U.S. Appl. No. 14/349,142, dated Mar. 27, 2015.
Office Action for U.S. Appl. No. 14/349,142, dated Jul. 28, 2015.
Office Action for U.S. Appl. No. 14/349,142, dated Mar. 25, 2016.
Office Action for U.S. Appl. No. 14/349,142, dated Nov. 25, 2016.
Written Opinion for PCT/SE2014/050380 dated Jul. 24, 2014.
Written Opinion for PCT/SE2012/051048, dated Jan. 30, 2013.
Office Action for U.S. Appl. No. 14/781,761 dated Sep. 29, 2016.
Office Action for U.S. Appl. No. 14/781,761 dated Apr. 13, 2017.

(Control blood was taken before 1st immunization)

NANOPARTICLES, PROCESS FOR PREPARATION AND USE THEREOF AS CARRIER FOR AMPHIPATIC AND HYDROPHOBIC MOLECULES IN FIELDS OF MEDICINE INCLUDING CANCER TREATMENT AND FOOD RELATED COMPOUNDS

This application is a continuation of and claims priority to U.S. application Ser. No. 14/349,142, filed Apr. 2, 2014, which is a 35 U.S.C. § 371 National Stage Application of International PCT Application No. PCT/SE2012/051048, filed on Oct. 1, 2012, which claims the benefit of U.S. Provisional Application No. 61/542,425, filed Oct. 3, 2011, applications which are incorporated herein by reference in their entirety.

FIELD OF INVENTION

The present invention regards nanoparticles comprising sterol and a component derived from *Quillaja saponaria* Molina selected from *quillaja* acid and *quillaja saponin*, which nanoparticles do not comprise a phospholipid as an essential component. It also relates to a composition comprising the nanoparticles, and the use thereof, as adjuvant, especially in vaccines and as agents for treatment of cancer, as carriers for amphipathic or hydrophobic molecules in the medical field especially for treatment of cancer and for food related compounds. Further, it regards a method for producing the phospholipid-free nanoparticles, a method for the treatment of cancer and a method for assessing the applicability of the cancer treating method and for making food related compounds soluble in water to promote their uptake by the body.

PRIOR ART

The Immune Stimulating Complex (ISCOM) is a 40 nm particle composed by saponin from the tree *Quillaja saponaria* Molina that firmly associates with cholesterol to form hexagonal rings with 6 nm diameter. The third component is a lipid e.g. phosphatidyle choline that glues the rings to form a 40 nm spheres. This particle is used with the specific vaccine antigens incorporated into the particle or as an adjuvant particle without an antigen co-administered with the vaccine antigen in a separate particle. The ISCOM particles may be produced with the method described by Lövgren & Morein and in EP 0 436 620 as well as in WO2004/004762.

One problem with the ISCOM and ISCOM Matrix is their complex production technology. That also raises problems to use it as a carrier/delivery system e.g. to integrate molecules/compounds to be passenger or to achieve complimentary effects for pharmacological and vaccine effects or as a targeting device.

Vaccines are mostly based on whole microorganisms or subunits that promote immune responses, including both antibody and T cell responses against surface structures. Alternatively, the vaccine antigens are subunits, i.e. most often the surface proteins, but also internal/intracellular proteins or even non-structural proteins being expressed in cellular vectors. Surface proteins and carbohydrate antigens are often valued for their capacity to evoke antibody responses, not excluding that they also induce cell mediated including T-cell responses, however, mostly not cytotoxic T-cell responses. Internal and non-structural proteins are used as vaccine antigens to evoke T cell responses including cytotoxic T-cells, since antibodies do not interact with internal proteins of the infecting agents and can, therefore, not mediate immune protection at the time point of infection. In contrast cell mediated immunity including T-helper cells and cytotoxic T-cells can kill infected cells i.e. after the time point of infection. Formulations and products of the ISCOM technology are used to enhance the immunogenicity of the accessible antigens i.e. surface antigens and the antigens revealed by the disruption (internal antigens) of the agent from which and against which the vaccine is prepared, cf Morein et al 2007[3] and WO2011/005183. Any vaccine antigen can also be produced by rDNA techniques and in many cases also synthetically produced as described by Lövgren & Morein[2]. The ISCOM technology is described in a number of patent applications, including US 2006/0121065 EP1539231A1, WO 2004/004762 and WO2005/002620).

Adjuvants in general are used to enhance level and quality of the immune responses of the antigens included in the vaccine formulation. However, there are a number of infectious agents that an unmet need is prevailing regarding protective vaccines and that (new) that immune protection is escaped by;

Escape mutants (human influenza virus, corona virus in chicken (infectious bronchitis virus [IBR]), hepatitis C virus (HCV)

Not revealing antigenic determinants
  Inaccessible-hidden (*staphylococcus aureus* [SA], *streptococcus equi*)
  Immune dominance by other antigenic determinants in the microorganism exemplified by influenza virus in man, parvovirus causing alution disease in mink, hepatitis C virus (HCV) in man.
  Inducing immune responses that exacerbate disease (parvovirus [alution disease] mink)
  Vaccines intended for species of pathogens having many to almost innumerable variants making it difficult/too costly alternatively making it more economical to produce a sufficiently covering vaccine e.g. HIV and Hepatitis C in man, It is also well-known that there are a number of vaccines that need several even as many as up to 23 vaccine components from the same number of strain variants e.g. carbohydrate variants (conjugate vaccines e.g. *Haemophilus influenzae, Meningococus miningitides, Streptococcus pneumonia, Streeptococcus pyogenes, Pneumococcus pneumonie* and also *Staphylococcus aureus*) having various capsule antigens.
  Other unmet needs prevails for various Gramm+ cocci e.g. *Staphylococcus* spp in animals particularly a need is required for vaccines protecting against mastitis in ruminants, caused by against *S aureus, Streptococcus* spp in horse (*Str. Equi, Str. Zooepidemicus*), in cattle (*Str. agalacti, Str. dysgalacti* and *Str. Uberis*)
  Antigenic sin (FLU) or carrier induced epitope suppression antigen (CIES).
  Fast replicating agents e.g. Human immune deficiency virus (HIV) complicates the escaping immune protective mechanisms of the host by new upcoming variants including those induced by vaccines.
  DNA and RNA vaccines lack in many cases adjuvants Thus, there is an unmet need to increase the capacity of vaccines to meet upcoming situations that e.g. lead to epidemics and even more to pandemics or to improve the possibility to keep protective value of a vaccine by evading negative effects of escape mutation or to compensate immunity lost by escape by mutation, or to enhance immune protection to upcoming variants due to mutations during the infection. For that reason also new particulate vaccine adjuvants may be required with the flexibility to adapt its steering of the immune response to an immunological profile required for protection against a particular pathogen.

Cancer is treated in various ways including surgery, irradiation and by pharmaceuticals i.e. cytostatic drugs. The medical treatment generally by cytostatic drugs cause severe side effects like irradiation therapy often causing severe side effects. Thus, there is an unmet need to have a medical treatment that is well tolerated by the patients. International patent publication WO2008/063129 and Hu et al', describes nanoparticles comprising cholesterol, phosphatidylcholine and *Quillaja* saponin fractions ASAP (acyl-saponin, corresponding to QS 21 or QHC) or DSAP (desacyl-saponin, corresponding to QS 7 or QHA). These particles named KGI and BBE are described to kill cancer cells at 30 to 40 fold lower concentrations than they are killing normal cells of similar origin as described in the invention "Killcan, New Use" in the patent application PCT/SE 2007/050878 and WO2008/063129 and Hu et al[1]. These particles have similar production complexity as those described for ISCOM and ISCOM Matrix.

Many potential pharmaceuticals cannot be developed because there solubility in water could not be achieved including their use in the fields of vaccine/adjuvant and drug delivery including anticancer pharmaceuticals. If such potential pharmaceuticals were taken from shelf and rendered soluble in water some of those would enrich the medical market.

SUMMARY OF THE INVENTION

The present inventors have identified a need for a new form of nanoparticle to be used as anticancer pharmaceutical, carrier/delivery particle for pharmaceuticals and as adjuvant that can compensate for the shortcoming of commercially available adjuvant-vaccine formulations.

A problem with the ISCOM technology is the complex procedure to formulate the particles based on detergent solubilisation of the *Quillaja* components, cholesterol and the third component e.g. phosphatidyl choline e.g. using ultra filtration, tangential flew, dialysis or centrifugation techniques. All of those techniques as described by Lövgren & Morein[2], cause loss of material during the production process.

Moreover, the ISCOM technologies are not readily suitable for integration of other hydrophobic or amphipathic molecules since methods so far developed allow the strong tendency of such compounds to spontaneously form stable complexes (self assembly) in water e.g. micelles not being integrated into the ISCOM formulation e.g. by hydrophobic interaction.

The present invention relates to a phospholipid-free nanoparticle comprising sterol and at least one saponin.

In contrast to the present invention, lipid containing particles such as liposomes, ISCOM, ISCOM MATRIX, posintros and various kinds of liposomes for the preparation and use in pharmaceuticals including adjuvant formulations to enhance the efficacy of vaccines and in vaccine formulations and formulations for treatment of cancer contains lipids like phospholipids e.g. phosphatidylserin and phosphatidylcholine, stearylamin etc.

The nanoparticles according to the invention may also be used as delivery systems for one or several compounds e.g. for pharmaceuticals including those used for treatment of cancer and nutrition related compounds where the additional substance(s) provide additional functions and complementary modes of action.

The advantage of the nanoparticles according to the invention merits them as replacements for the prior art formulations including a broadened application as adjuvants to cover new variants of a pathogen e.g. upcoming pandemics described above.

The present invention provides an easy production process with virtually no losses, due to the evaporation technology. That does not exclude the use of techniques as described for the production of ISCOMs or ISCOM Matrix (see above).

Aspects of the invention are described in the independent claims. Preferred embodiments are set forth in the dependent claims.

SHORT DESCRIPTION OF THE APPENDED DRAWINGS

Figure 1B:
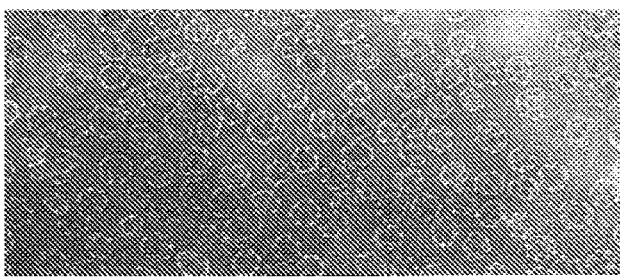

FIG. 1 A. The electron microscopy (EM) shows a nanoparticle comprising cholesterol, QHC and diterpenoid in a molar ratio of 1:1:0.5. The particles have a mean diameter of about 17-20 nm according to the invention. It is distinctly different from an ISCOM particle of about 40 nm as depicted in FIG. 1B. Particles according to the invention without the diterpenoid have the same morphology.

FIG. 1B. The electron microscopy shows an ISCOM like particle comprising cholesterol, QHC and phosphatidylcholin in a molar ratio: 1:1:0.5. The particles is prepared as described using a technology similar to that described in Example 1 according design C in Example 1 have a diameter of about 40 nm i.e. using the. The morphology and size are distinctly different from those of a nanoparticle according to the invention as depicted in FIG. 1A.

Figure 2:
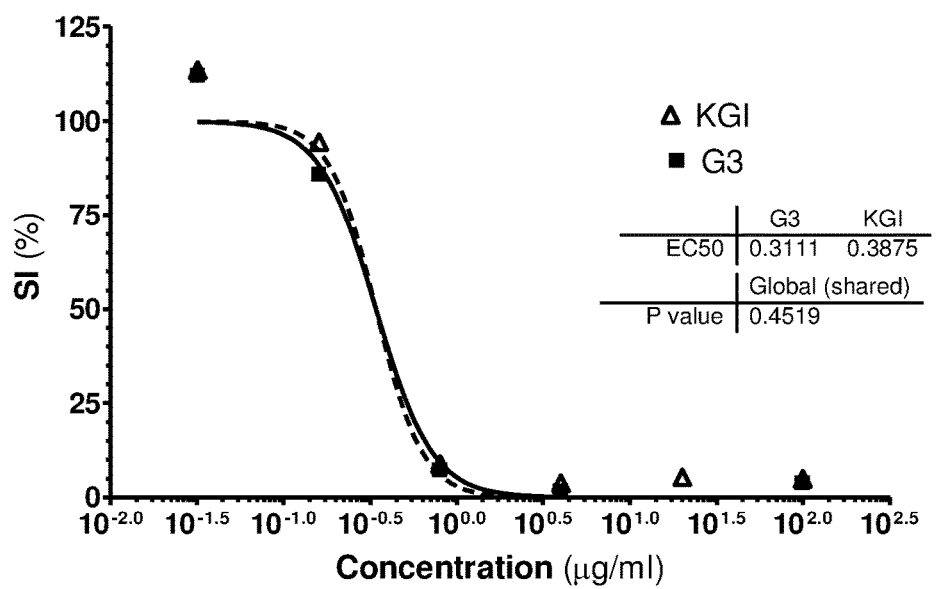

FIG. 2. Comparison of cancer cell killing capacity between G3 and KGI nanoparticles both containing QHC tested on U937 cells. G3 and KGI have virtually the same anti-cancer cell killing effect on the model tumour cell (P=0.8422).

Figure 3:
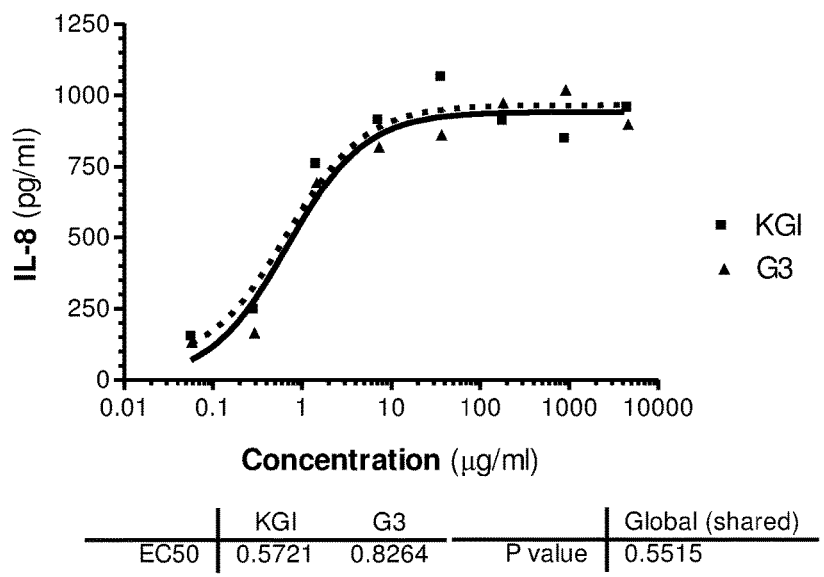

FIG. 3. Comparison of G3 with KGI to inducing U937 tumour cells to produce IL-8 showing that both particles have similar capacity to induce cancer cells to produce cytokine indicating cancer cell differentiation (P>0.05).

Figure 4A:
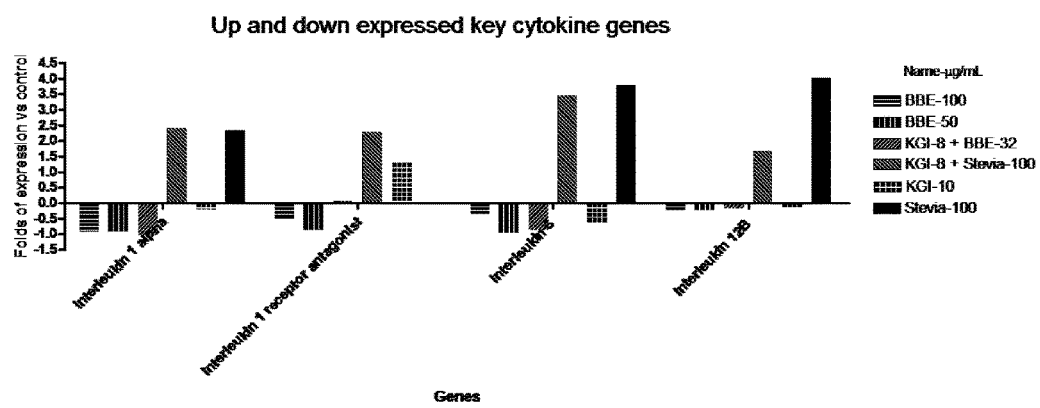

FIG. 4A. *Stevia* is the strongest inducer of IL-12B, IL-6 and IL-1 alpha compared to BBE or KGI.

Figure 4B:
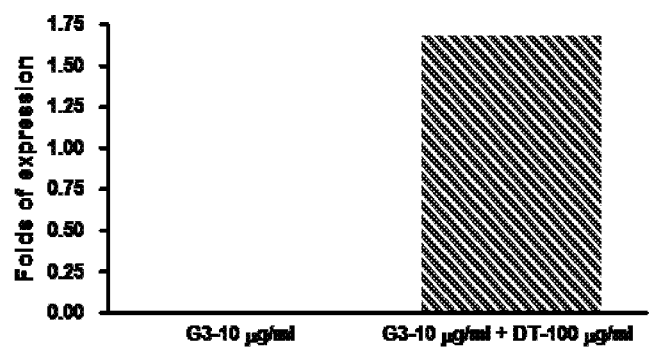

FIG. 4B. DT, when incorporated into G3, up-regulates cytokine IL-12 gene expression of normal human DCs.

Figure 5:
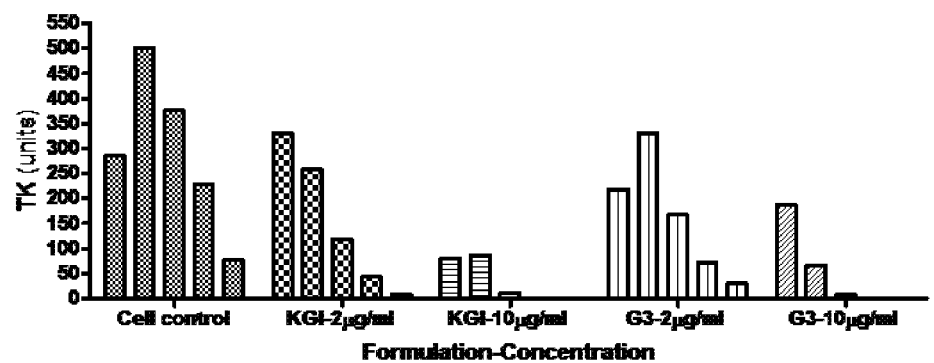

FIG. 5. G3 particles influence intra-cellular TK production of U937 cells at a similar magnitude to that of KGI particles (the bars in each formulation-concentration combination indicates time points of 24, 48, 72, 96 and 120 hours from the left to the right).

Figure 6:
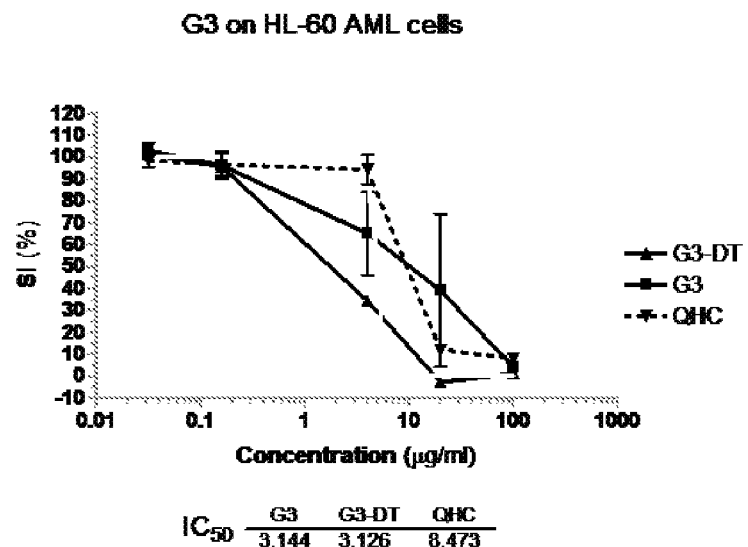

FIG. 6. The titration curves of G3, G3 with DT incorporated (G3-DT) and non-particulate QHC read on HL-60 AML cells. The G3 and G3-DT formulations kill the AML cells more efficiently than free non-particulate QHC FIG. 7. The stand alone and combination effects of G3 and cytarabine on HL-60 AML cells. G3 enhances the significantly the cytarabine FIG. 8. G3 enhances the killing capacity of daunorubicin on HL-60 AML cancer cells FIG. 9. The titration curves of G3, G3 with DT incorporated (G3-DT) and QHC on PC-3 prostate cancer cells FIG. 10. The stand alone and combination effects of G3 and docetaxel on PC-3 prostate cancer cells. The G3 enhances significantly the cancer cell killing effect of docetaxel FIG. 11. G3 enhances the killing effect of cabazitaxel on PC-3 prostate cancer cells FIG. 12. The titration curves on ACHN kidney cancer cells show that G3 formulated with QHA is more potent ($P<0.01$) than G3 formulated with QHA in killing the solid cancer cells.

Figure 13A:
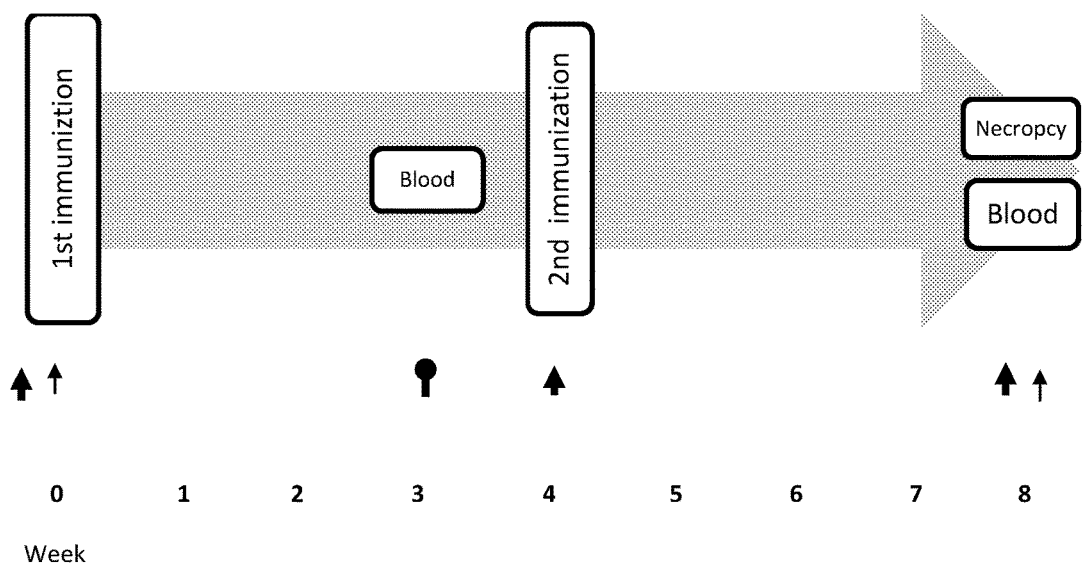

FIG. 13A. Immunization schedule

Experimental design (C56Bl6 mice, 6 mice/group, 200 μl/dose, s.c. two immunizations, 4 weeks apart)

Group 1 (Abisco Control): Influenza 1 μg+ISCOM–5 μg
Group 2 (G3-High Dose): Influenza 1 μg+G3–5 μg
Group 3 (G3-Midium Dose): Influenza 1 μg+G3–2.5 μg
Group 4 (G3-Low Dose): Influenza 1 μg+G3–1 μg
Group 5 (G3 with DT): Influenza 1 μg+G3–2.5 μg
Group 6 (Non-adjuvanted, Antigen Control): Influenza 1 μg
Group 7 (Non-immunized Control)

Evaluation

Blood for antibody responses. Spleen cells at necropsy for cell-mediated immunity including proliferation test, IL-4, IFN-γ.

Figure 13B:
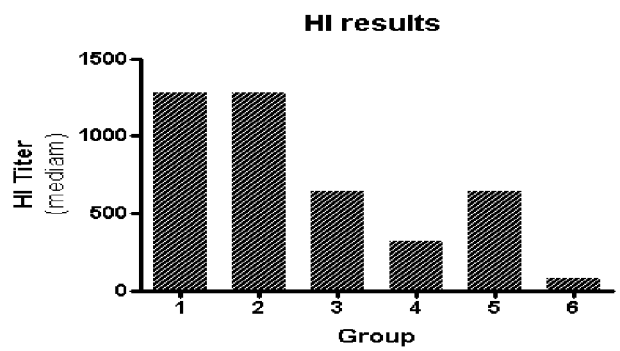

FIG. 13B. HI antibody response of mouse serum measured at 3 weeks after the $1^{st}$ immunization FIG. 13C. HI antibody response of mouse serum measured at 4 weeks after the $2^{nd}$ immunization FIG. 13D. Cytokine responses of mouse spleen cells at 4 weeks after the $2^{nd}$ immunization FIG. 14A. The G3/VLX40 formulation (the right column) has high cancer cell (U937) killing effect. In contrast to VLX40 alone (the left column) had low cancer cell killing effect indicating high solubility of G3/VLX40 formulation and low cancer cell killing effect of the VLX40-DMSO formulation FIG. 14B. VLX40 DMSO formulation (left column) has high anticancer activity in the precipitates. In contrast the scanty precipitate of the G3-VLX40 (right column) formulation had low anticancer cell activity indicating that the anticancer cell activity essentially was located to the water phase.

DEFINITIONS

All terms and words in the present specification shall be construed as having the meaning usually given to them in the relevant art unless specifically indicated otherwise. For the sake of clarity, a few terms are defined below.

A vaccine formulation is a pharmaceutical formulation that is used prophylactically and improves/enhances protective immunity to/against one or more particular diseases. A therapeutic vaccine according to the invention can be used to cure disease when an antigen specific for a component connected to the disease is included in the formulation with the invention or, as is particular for cancer treatment, the antigen is present in the cancer/tumor. A vaccine includes an "antigen" that elicits an immune response in the treated subject and, optionally, a substance added to a vaccine to improve the immune response called an "adjuvant".

An "antigen" is thus the active specific part in a vaccine and may be the entire micro-organism, such as virus or bacteria, causing the disease that the vaccine is aimed at improving immunity to. It may also be a part of said micro-organism a subunit, such as a protein (a sub-unit) a part of a protein, a protein either isolated from the pathogenic microorganism or produced by rDNA technique or synthetically produced then often called peptide. A peptide has fewer amino acids than a protein.

An "adjuvant" is a vaccine constituent that enhances the level and or the quality of the immune response to the antigen part of the prophylactic or therapeutic vaccine.

A nutrition related compound is any compound related to nutrient including vitamins health active substances taste improving compounds.

DETAILED DESCRIPTION OF THE INVENTION

The present invention relates to nanoparticles comprising sterol and a component from *Quillaja saponaria* Molina selected from *quillaja* acid and *quillaja* saponin, characterized in that said nanoparticles do not comprise a phospholipid.

The resulting particle according to the innovation differs from ISCOMs with regard to size, wherein the particles according to the invention are below 40 nm, around-20 nm whereas ISCOMs are ~40 nm. Thus, the nano particle of the invention may have a diameter in the range of 10-40 nanometers, preferably 12-35 nanometers or 15-25 nanometers. The size will to an extent dependent on the load of integrated other molecules than cholesterol and the *quillaja* molecule The sterol may be selected from cholesterol, cholestanol, caprostanol, phytosterols, e.g. stigmasteroll sitosterol, mycosterols, e.g. ergosterol, preferably cholesterol and vitamin D3 or any hydrophobic compound the is exposed in water to react covalently with reactive group in the water souble including suspension in water of a micelle.

*Quillaja* saponin or any of its fractions with a common triterpenoid skeleton also named *Quillaja* acid may be used. There are so far 4 forms of *quillaja* acids described. *Quillaja* saponins are forming chains with a number of sugars either with an acyl group i.e. an acyl-saponin (ASAP) or without the acyl chain i.e. desacyl-saponin (DSAP) as described in e.g. Hu et al.[1]

The saponin may be hydrophilic and selected from fractions 4, 5, 6, 7, 8, 9, 10, 11, 12, 13, 14 and 15 of Quil A, especially fractions 7, 8, 9, 10, 11, 12, 13 and 14 described in EP 0 3632 279 B2 and fraction A of Quil A or crude Quil A.

The saponine may be a crude or raw, or non-fractionated extract of Quil A comprising a mixture of saponins or a semi purified forms thereof such as *Quillaja* Powder Extract (Berghausen, USA), *Quillaja* Ultra Powder QP UF 300, *Quillaja* Ultra Powder QP UF 1000 or Vax-Sap (all three from Natural Responses, Chile) or from Prodalysa, Santiago, Chile. The purified saponin fractions C and B solitary or combined together with may be used. The B and C fractions are described in WO 96/11711, the B3, B4 and B4b fractions described in EP 0 436 620. The fractions QA1-22 described in EP 0 3632 279 B2, Q-VAC (Nor-Feed, AS Denmark), *Quillaja Saponaria* Molina Spikoside (Isconova A B, Uppsala Science Park, 751 83, Uppsala, Sweden).

The saponin may be hydrophobic saponin and selected from saponins that do contain fatty acids e.g. in the 4-position in the triterpenoid aglycone of the saponins from *Quillaja Saponaria* Molina such as fraction C and B of Quil A or fractions from the region between fractions A and B and fractions 15, 16, 17, 18, 19, 10 and 21 described in EP 0 3632 279 B2, especially fractions 17 and 18 are suitable here. Preferably *quillaja* saponin fraction QHA, QHB and/or QHC may be used.

The ratio between cholesterol and *quillaja* saponin may be from 1:10 to 10:1, preferably from 1:2 to 2:1.

The nanoparticles according the invention may further comprise at least one an amphipathic or a hydrophobic molecule, which may be selected from an antigen, an adjuvant, a targeting molecule, a pharmaceutical compound and a food related compounds.

The antigen may be any antigen with amphipathic or a hydrophobic groups as described in EPC-patent application 0 109 942, or rendered to have a hydrophobic region by rDNA expression and produced by cells or chmically sythesized. The adjuvant may be any adjuvant with amphipathic or hydrophobic groups such as those obtained from *Quillaja saponaria* Molina.

One or more compounds molecules may be incorporated into G3 for complementary functions e.g. as targeting device or as antigen or complementary antigens in the use of vaccines for immune modulatory functions described in EP 9600647-3(PCT/SE97/00289 or as pharmaceutical including anticancer or nutritional effects. To be incorporated into G3 particles the molecules require hydrophobic domains or are electrostatic attached to the G3 particles. Compounds that do not have hydrophobic portions may be coupled to molecules having such molecules before or after incorporation into the G3 particle as described for a similar particle in EP 1800564.

Any adjuvant may be incorporated such as, natural or synthetic including synthetic or semi synthetic *quillaja* saponin or saponin fractions or derivates thereof from *Quillaja saponaria* Molina, lipid A or derivates or synthetic versions thereof, cell wall skeleton but not limited to mentioned adjuvant compounds. A Diterpenoid (DT) supplied by Javier Saints, Prodalysa, Santiago, Chile may be used as an adjuvant and a nutritional (from *stevia* a sweetening agent). The diterpenoid (DT) has been integrated into the nanoparticles according to the invention resulting in typical small nanoparticles of 17 nm.

Lipid-containing receptors that bind to cell-binding components, including cholera toxin's receptor, which is the ganglioside GM1, and fucosed blood group antigen may be used. The cell-binding components can also function as mucus targeting molecule. The technology for complexes comprising are described in e.g. WO97/30728 and can be applied to G3 particle both for anticancer treatment and for vaccine use. Any subfragment of *Quillaja saponaria* Molina may be used solitary or in various combinations. Receptors supplied with hydrophobic tail/region intended to capturing molecules to the invented particle to supply desired complementary properties e.g. different mode of cancer cell killing e.g. monoclonal antibodies that both target cancer cells and also have cell killing effect is one carrier-delivery option.

Thus other components that may be integrated into the nanoparticle are pharmaceuticals including anticancer drugs including receptors for antibodies or monoclonal antibodies such as Fc receptors or the DD of Protein A of *Staphylococcus aureus* (WO2011/005183).

The production method of nanoparticles disclosed by the present invention is simpler than for ISCOM and more suited to incorporate hydrophobic and amphipathic molecules. Thus, the inventive nanoparticle is a nanoparticle suited for delivery of vaccine antigens, drugs for anticancer treatment as well as for any kind of drug. The particle produced as described herein can also be supplemented with integrated amphipathic molecules (lipids such as stearylamine etc.) to be used for covalent linking other molecules e.g. drugs or vaccine antigens, or for electrostatic linking, lectin linking as described Morein etc[3]. and in WO2004/004762.

The particle may further comprise cancer targeting molecules such as surface antigens from cancer cells, virus surface antigens and influenza antigens.

Surface molecules from microbial membranes may be incorporated by hydrophobic interaction as originally described by Morein et al[a] and in EP 242380. Other molecules e.g. produced by rDNA technology or synthetically produced can be incorporated as described in WO 2002/080981 and WO 2004/030696.

Such targeting molecules include envelop proteins from viruses such as influenza and respiratory syncytial viruses having affinity to respiratory tract e.g. to target forms of lung cancer, or CTA1DD being the A1 part of the A subunit of cholera toxin incorporated into KGI or BBE formulations as described by Lycke et al[4]. CTA1DD is rationally designed of three main components, each contributing complementary effects. CTA1 is the enzymatically active subunit of cholera toxin that is converted non-toxic by separation from the A2 and B subunits. Fused to DD from protein A from *Staphylococcus aureus* it targets B cells. More generally, mono and polyclonal antibodies can be incorporated into the particles as described in EP 0 109 942 B1, EP 0 242 380 B1 and EP 0 180 564 B1.

The invention also regards a composition comprising one or more nanoparticles. The composition may comprise different *quillaja* saponin fractions each incorporated in different nanoparticles.

Thus, two different saponin fractions may be complex bound in one G3 particle and the other one (the other ones) of the at least two different saponin fractions is (are) complex bound in another(other) physical different lipid containing particle(s).

The different saponins may be hydrophilic and hydrophobic saponins respectively. The particle may contain at least fraction C or at least fraction B or at least any fraction between fraction C and B of Quil A and at least one other fraction of Quil A. Thus one particle may comprise fraction C only; fraction C and at least one other fraction of Quil A; fraction C and one or more fractions of Quil A; fraction C and fraction A of Quil A; crude Quil A. The particle may also contain fraction B only; fraction B and at least one other fraction of Quil A; fraction B and one or more fractions of Quil A; fraction B and fraction A of Quil A. The above combinations of fractions may also be in different lipid particle or in the same lipid particle.

Thus, mixtures of lipid containing particles comprising hydrophilic and hydrophobic saponins in physically different particles may be used.

According to one embodiment the fraction A of Quil A may be integrated into a nano particle together with at least one other adjuvant with immunomodulating activity.

According another embodiment the at least one other adjuvant is present in free form or integrated into another separate nano particle for the preparation of an adjuvant composition.

The at least one other adjuvant may be a saponin such as a Quil a saponin.

Fraction A may facilitates the use of another adjuvant which when used by itself might be toxic in doses it is efficient and a synergistic effect including enhancement of immune responses and immunomodulating activity may be obtained.

A composition according to the invention may comprise the adjuvant fraction A from Quil A and the at least one other adjuvant in any weight ratios. Preferably fraction A of Quil A is from 2-99.9 weight %, preferably 5-90 weight % and especially 50-90 weight % counted on the total amount of adjuvants. For e.g. Al(OH)$_3$, oil adjuvants and block polymers the amount of fraction A, of Quil A may be substantially lower.

One preferred iscom composition comprises 50-99.9% of fragment A of Quil A and 0.1-50% of fragment C and/or fraction B and/or other fractions or derivatives of Quil A (hereinafter non-A Quil A fractions) counted on the total weight of fractions A and non-A Quil A fractions. Especially the composition comprises 70-99.9% of fragment A of Quil A and 0.1-30% of non-A Quil A fractions, preferably 75-99.9% of fragment A of Quil A and 0.1-25% of non-A Quil A fractions and especially 80-99.9% of fragment A of Quil A and 0.1-20% of non-A Quil A fractions counted on the total weight of fraction A and non-A Quil A fractions. Most preferred composition comprises 91-99.1% of fragment A of Quil A and 0.1-9% of non-A Quil A fractions counted on the total weight of fractions A and non-A Quil A fractions, especially 98.0-99.9% of fraction A and 0.1-2.0% of non-A Quil A fractions counted on the total weight of fractions A and non-A Quil A fractions.

The nanoparticles and a composition comprising the nanoparticles may be used as a pharmaceutical optionally in a pharmaceutical composition further comprising pharmaceutically acceptable buffers, diluents excipients, additives, adjuvants and/or carriers.

Suitable pharmaceutically acceptable carriers and/or diluents include any and all conventional solvents, dispersion media, fillers, solid carriers, aqueous solutions, coatings, antibacterial and antifungal agents, isotonic and absorption delaying agents, and the like. The use of such media and agents for pharmaceutically active substances is well known in the art, and it is described, by way of example, in Remington's Pharmaceutical Sciences, 18th Edition, Mack Publishing Company, Pennsylvania, and USA. Except insofar as any conventional media or agent is incompatible with the active ingredient, use thereof in the pharmaceutical compositions of the present invention is contemplated. Supplementary active ingredients can also be incorporated into the compositions.

The invention also comprises a pharmaceutical composition further comprising at least one pharmaceutically active compound, such as anticancer drugs, platinum coordination compounds, taxane compounds, camptothecin compounds, anti-tumour vinca alkaloids, anti-tumour nucleoside derivatives, nitrogen mustard or nitrosourea alkylating agents, anti-tumour anthracycline derivatives, trastzumab and anti-tumour podophyllotoxin derivatives, *Quillaja saponaria* Molina and sub fragments thereof, receptors for antibodies or monoclonal antibodies such as Fc receptors or the DD of Protein A of *Staphylococcus aureus*, agents for treating cancer, such as agents selected from the group consisting of Cytarabin, Daunorubicin, Paclitaxel, Docetaxel, Cabazitaxel, Toricsel and Trabectidin, which active compound may be integrated into the nanoparticle or mixed with the composition.

The further anti-cancer agents are preferably selected from namely platinum coordination compounds, taxane compounds, camptothecin compounds, anti-tumour vinca alkaloids, anti-tumour nucleoside derivatives, nitrogen mustard or nitrosourea alkylating agents, anti-tumour anthracycline derivatives, trastzumab and anti-tumour podophyllotoxin derivatives.

The term "platinum coordination compound" is used herein to denote any tumour cell growth inhibiting platinum coordination compound which provides platinum in the form of an ion. Preferred platinum coordination compounds include cisplatin, carboplatin, chloro (diethylenetriamine)-platinum (II) chloride; dichloro (ethylenediamine)-platinum (II); diamine (1, 1-cyclobutanedicarboxylato)-platinum (II) (carboplatin); spiroplatin; iproplatin; diamine (2-ethylmalonato)-platinum (II); (1, 2-diaminocyclohexane) malonato-platinum (II); (4-carboxyphthalo) (1, 2-diaminocyclohexane) platinum (II); (1, 2-diaminocyclohexane)-(isocitrato) platinum (II); (1, 2-diaminocyclohexane)-cis-(pyruvato) platinum (II); and (1, 2-diaminocyclohexane)-oxalato-platinum (II); ormaplatin and tetraplatin.

Cisplatin is commercially available for example under the trade name Platinol from Bristol Myers Squibb Corporation as a powder for constitution with water, sterile saline or other suitable vehicle. Other platinum coordination compounds and their pharmaceutical compositions are commercially available and/or can be prepared by conventional techniques.

The taxane compound may be those sold under the trade name Taxol from Bristol Myers Squibb and docetaxel is available commercially under the trade name Taxotere from Rhone-Poulenc Rorer. Both compounds and other taxane compounds may be prepared in conventional manner for example as described in EP 253738, EP 253739 and WO 92/09589 or by processes analogous thereto. Carbazitaxel available from Sanofi Pasteur.

Camptothecin compounds include irinotecan and topotecan. Irinotecan is commercially available for example from Rhone-Poulenc Rorer under the trade name Campto and may be prepared for example as described in European patent specification No. 137145 or by processes analogous thereto. Topotecan is commercially available for example from SmithKline Beecham under the trade name Hycamtin and may be prepared for example as described in European patent specification No. 321122 or by processes analogous thereto. Other camptothecin compounds may be prepared in conventional manner for example by processes analogous to those described above for irinotecan and topotecan.

Anti-tumour vinca alkaloids include vinblastine, vincristine and vinorelbine referred to above. Vinblastine is commercially available for example as the sulphate salt for injection from Eli Lilly and Co under the trade name Velban, and may be prepared for example as described in German patent specification No. 2124023 or by processes analogous thereto. Vincristine is commercially available for example as the sulphate salt for injection from Eli Lilly and Co under the trade name Oncovin and may be prepared for example as described in the above German patent specification No. 2124023 or by processes analogous thereto.

Vinorelbine is commercially available for example as the tartrate salt for injection from Glaxo Wellcome under the trade name Navelbine and may be prepared for example as described in U.S. Pat. No. 4,307,100, or by processes analogous thereto Other anti-tumour vinca alkaloids may be prepared in conventional manner for example by processes analogous to those described above for vinoblastine, vincristine and vinorelbine.

Anti-tumour nucleoside derivatives include 5-fluorouracil, gemcitabine and capecitabine referred to above. 5-Fluorouracil is widely available commercially, and may be prepared for example as described in U.S. Pat. No. 2,802,005. Gemcitabine is commercially available for example from Eli Lilly under the trade name Gemzar and may be prepared for example as described in European patent specification No. 122707 or by processes analogous thereto.

Capecitabine is commercially available for example from Hoffman-La Roche under the trade name Xeloda and may be prepared for example as described in European patent specification No. 698611 or by processes analogous thereto.

Other anti-tumour nucleoside derivatives may be prepared in conventional manner for example by processes analogous to those described above for capecitabine and gemcitabine.

Nitrogen mustard compounds include cyclophosphamide and chlorambucil. Cyclophosphamide is commercially available for example from Bristol-Myers Squibb under the trade name Cytoxan and may be prepared for example as described in U. K. patent specification No. 1235022 or by processes analogous thereto. Chlorambucil is commercially available for example from Glaxo Welcome under the trade name Leukeran and may be prepared for example as described in U.S. Pat. No. 3,046,301, or by processes analogous thereto. Preferred nitrosourea compounds for use in accordance with the invention include carmustine and lomustine referred to above. Carmustine is commercially available for example from Bristol-Myers Squibb under the trade name BiCNU and may be prepared for example as described in European patent specification No. 902015, or by processes analogous thereto. Lomustine is commercially available for example from Bristol-Myers Squibb under the trade name CeeNU and may be prepared for example as described in U.S. Pat. No. 4,377,687, or by processes analogous thereto.

Anti-tumour anthracycline derivatives include daunorubicin, doxorubicin and idarubicin referred to above. Daunorubicin is commercially available for example as the hydrochloride salt from Bedford Laboratories under the trade name Cerubidine, and may be prepared for example as described in U.S. Pat. No. 4,020,270, or by processes analogous thereto.

Doxorubicin is commercially available for example as the hydrochloride salt from Astra, and may be prepared for example as described in U.S. Pat. No. 3,803,124 or by processes analogous thereto. Idarubicin is commercially available for example as the hydrochloride salt from Pharmacia & Upjohn under the trade name Idamycin, and may be prepared for example as described in U. S patent specification No. 4046878 or by processes analogous thereto Other anti-tumour anthracycline derivatives may be prepared in conventional manner for example by processes analogous to those described above for daunorubicin, doxorubicin and idarubicin.

Trastzumab is commercially available from Genentech under the trade name Herceptin and may be obtained as described in U. S. Patent specification No. 5821337 or PCT patent specifications WO 94/04679 and WO 92/22653.

Anti-tumour anti-tumour podophyllotoxin derivatives include etoposide and teniposide. Etoposide is commercially available for example from Bristol-Myers Squibb under the trade name VePesid, and may be prepared for example as described in European patent specification No. 111058, or by processes analogous thereto. Teniposide is commercially available for example from Bristol-Myers Squibb under the trade name Vumon and may be prepared for example as described in PCT patent specification No. WO 93/02094, or by processes analogous thereto. Other anti-tumour podophyllotoxin derivatives may be prepared in conventional manner for example by processes analogous to those described above for etoposide and teniposide.

Saponins in crude form or fractions thereof such as those mentioned above may also be used in free form, i.e. not integrated into lipid comprising particles, as anti-cancerous agents. These anticancer compounds may be mixed with, coupled on to or integrated into the lipid containing particles such as liposomes, iscom and/or iscom matrix and posintros.

It is suitable if they are hydrophobic when integrated. If not hydrophobic groups may be coupled on to them as described in EP 242380.

Non-hydrophobic compounds and especially proteins or peptides may be rendered hydrophobic by coupling hydrophobic groups to them.

The hydrophobic group that can be coupled to the non-hydrophobic compounds are straight, branched, saturated or unsaturated aliphatic chains, preferably having 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 carbon atoms, or hydrophobic amino acids or peptides or other hydrophobic structures such as steroids. The length of the hydrophobic structure is adapted to the size and nature of the protein. As an example, it can be mentioned that a peptide with 10-15 amino acids (foot-and-mouth disease virus) suitably is brought out with two tyrosine at the amino or carboxy terminal end. A protein with a molecular weight of 70,000 daltons demands about 20 hydrophobic amino acids. Testing is made empirically. Thus, one uses especially peptides with 1 to 20 amino acids, preferably 1, 2, 3, 4, 5 amino acids, especially chosen among Trp, Ile, Phe, Pro, Tyr, Leu, Val, especially Tyr; cholesterol derivatives such as choline acid, ursodesoxycholine acid.

These hydrophobic groups must be bonded to a group that can be coupled to the non-hydrophobic protein or compounds such as carboxyl-, amino-, disulphide-, hydroxyl-, sulohydryl- and carbonyl group, such as aldehyde groups.

As hydrophobic groups that can be coupled are selected preferably carboxyl, aldehyde, amino, hydroxyl, and disulphide derivatives of methan, ethane, propane, butane, hexane, heptane, octane and peptides containing Cys, Asp, Glu, Lys, preferably octanal and Tyr.Tyr.Tyr-Cys,-Asp or -Glu. The hydrophobic groups with a group that can be coupled must be dissolved in water with the aid of for example the solubilising agents and detergents mentioned above or hydrochloric acid, acetic acid 67% by volume acetic acid, caustic liquor, ammonia, depending on what substance is to be dissolved. pH is then adjusted to the neutral direction without the substance precipitating; here it is to make sure that there is not obtained a pH value that denaturates the protein to which the hydrophobic group is to be coupled. Lipid may enhance the solubilisation.

The hydrophobic molecule may be added to the non-hydrophobic compound in the molar ratio of 10:1 to 0.1:1, preferably 1:1.

Hydrophobic groups with a carboxyl group as coupling molecule can be coupled to the protein through water-soluble carbodiimides or composite anhydrides. In the first case the carboxyl group is activated at pH 5 with carbodiimide and mixed with the protein dissolved in buffer pH 8 with a high phosphate content. In the latter case the carboxy compound is reacted with isobutylchloroformate in the presence of triethylamine in dioxane or acetonitrile, and the resulting anhydride is added to the protein at pH 8 to 9. It is also possible to convert the carboxyl group with hydrazine to hydrazide which together with aldehydes and ketones in periodate-oxidized sugar units in the protein gives hydrazone bonds.

The amino groups with nitrous acid can at a low temperature be converted to diazonium salts, which gives azo bonds with Tyr, His and Lys. The hydroxyl groups with succinic anhydride can be converted to hemisuccinate derivatives which can be coupled as carboxyl groups. Aldehyde groups can be reacted with amino groups in the protein to a Schiff's base. Several coupling groups and methods are described[6,7,8].

The proteins, peptides or compounds so produced having received hydrophobic groups are then complex-bonded with glycoside, as described in a), but here the purification steps for removing cell fragments can be omitted.

Hydrophilic proteins having enclosed hydrophobic groups can be rendered hydrophobic by making the hydrophobic groups accessible by gently denaturating the proteins, i.e. with a low pH of about 2.5, 3M urea or at a high temperature above 70.degree. C. Such proteins may be immunoglobulines such as IgG, IgM, IgA, IgD and IgE. The immunoglobulines can be used as antidiotypic antibodies. The proteins are obtained purified as proteins as described in (b) and then complex-bonded to glycoside as described in (a), the purification steps for removing cell fragments being omitted.

The hydrophobic or amphiphatic molecule may also be chosen from phospholipides such as derivatives of glycerol phosphates such as derivatives of phosphatidic acids i.e. lecithin, cephalin, inositol phosphatides, spingosine derivatives with 14, 15, 16, 17, 18, 19 and 20 carbon atoms, phosphatidylethanolamine, phophatidylserine, phosphatidyl choline.

All above mentioned amphipathic and hydrophobic molecule, which may be selected from an antigen, an adjuvant, a targeting molecule, a pharmaceutical compound and a nutriment may be integrated into the nanoparticle or mixed therewith in a composition.

The pharmaceutical composition may be used as an adjuvant, e.g. for use in combination with a vaccine under development, for use in combination with a seasonal influenza virus vaccine, for use in combination with a pandemic influenza vaccine or for use in combination with an emergency vaccine, such as a vaccine against a biological weapon. Thus, the invention also regards a pharmaceutical vaccine formulation comprising the G3 particles as mentioned above.

The invention also relates to a method for treating or preventing a disease caused or complicated by an organism, comprising administering to a subject a pharmaceutical vaccine formulation according to the invention to a person in need thereof.

Further, the invention regards a method for treatment of cancer, comprising administering to a patient in need thereof a pharmaceutically effective amount of nanoparticles or a composition according to the invention. According to one embodiment the said cancer is leukemia.

The pharmaceutical compositions may be in the form of a sterile injectable aqueous or oleaginous suspension. This suspension may be formulated according to the known art using those suitable dispersing or wetting agents and suspending agents, which have been mentioned above. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The solutions or suspensions could also comprise at least one of the following adjuvants: sterile diluents such as water for injection, saline, fixed oils, polyethylene glycols, glycerol, propylene glycol or other synthetic solvents, antibacterial agents such as benzyl alcohol or methyl paraben, antioxidants such as ascorbic acid or sodium bisulfite, chelating agents such as ethylene diamine tetraacetic acid, buffers such as acetates, citrates or phosphates, and agents for adjustment of the tonicity such as sodium chloride or dextrose. The parenteral preparation could be enclosed in ampoules, disposable syringes or multiple dosage vessels made of glass or plastic.

The compounds of general formula may be administered parenterally. The term parenteral as used herein includes subcutaneous injections, intravenous, intramuscular, intradermal injection of infusion techniques, electroporation (EP), for needle less injection—jet injection, gene gun, biljector as well as oral, aerosol administrations. For oral use e.g. protein A derived compound CTA1DD may be used as described by Eliasson et al.[9] having a property to targeting B-cells useful treating-cells for induction of mucosal immunity particularly in the intestinal tract but also potentially also for cancers particularly for B-cells lymphoma.

Generally, the lipid containing particles of this invention are administered in a pharmaceutically effective amount. The amount of the particles actually administered will be typically determined by a physician, in the light of the relevant circumstances, including the condition to be treated, the chosen route of administration, the actual compound administered, the age, weight, and response of the individual patient, the severity of the patient's symptoms, and the like.

The nanoparticle according to the invention may be used as an adjuvant in any vaccine against any microorganisms. I may be used on any animal such as birds, mammals such as humans, domestic animals such as cats, dogs, sheep, goat, pigs, cattle and horses. According to one embodiment the invention is used as adjuvant in a vaccine against streptococci in animals and influenza in horses.

Doses for human use may vary according to other compounds included. In view of duration of treatment the dose may range from <50 μg to 1 mg or more per day.

The invention also regards a method for assessing the applicability of the method for treatment of cancer according to the invention to an individual patient, comprising
bringing cancer cells from said patient in contact in vitro with nanoparticles comprising sterol, preferably cholesterol, and a component from Quillaja saponaria Molina selected from quillaja acid and quillaja saponin, characterized in that said nanoparticles do not comprise a phospholipid or a pharmaceutical composition the nanoparticles and further comprising pharmaceutically acceptable buffer, diluents excipients, adjuvants and/or carriers;
measuring at least one effect indicative of therapeutic effect of said nanoparticles or pharmaceutical composition on said cancer cells;
wherein the method for treatment of cancer, optionall leukemia, comprising administering to a patient in need thereof a pharmaceutically effective amount of the nanoparticles or the pharmaceutical composition is assessed as applicable to said individual patient if the nanoparticles or pharmaceutical composition shows a significant effect indicative of therapeutic effect on said cancer cells.

The indication of therapeutic effect can be read by down regulation of genes, which have importance in the cell cycle regulation as cycline dependent kinases (CDKs), cyclins or other molecules promoting passage over check points in the cell cycle and replication (CDK2, CDK6 and CyclineD1) or down regulation of thymidine kinase (TK) and upregulation of molecules facilitating the cell differentiation, as IL-8, FOXC1 and HDAC5 also indicating exit from the cell cycle.

The regulation factors are examples and there are more i.e. the examples does not conclude limitations.

The invention also regards a method for producing phospholipid-free nanoparticles comprising the steps a) providing a hydrophobic surface or a suspension of liposomes
b) bringing hydrophobic surface or the suspension of liposomes into contact with a solution of sterol, preferably cholesterol dissolved as monomers in an organic solvent or detergent;
c) removing the solvent or detergent forming a sterol membrane on the surface
d) providing a water solution of *quillaja* saponin micelles
e) adding the water solution comprising the saponin micelles to the sterol membrane, whereby a complex is formed between the saponines and the sterols and is suspended in the water solution.

The hydrophobic surface might be a surface in a jar, tub, several layer surfaces, beads, e.g. latex beads, nets or three dimensional nets or porous material. It might also be a liposome with the components integrated in the lipid membrane(s).

The liposome can be constructed according various techniques and with different compositions as described (e.g. in Review Liposomes Preparation Methods Mohammad Riaz Faculty of Pharmacy, University of the Punjab, Lahore, Pakistan Pakistan Journal of Pharmaceutical Sciences Vol. 19(1), January 1996, pp. 65-77). It might also be constructed as a virosome containing virus proteins integrated in the liposome membrane. The liposomes may be in a water solution. The devices may e.g. be packed in columns.

The saponins and sterols may be the ones mentioned above for the nanoparticles

The solvent may be any solvent as may be found on the site http://en.wikipedia.org/wiki/Organic solvents or detergent, preferably chloroform, ethanol or acetonirtril. The nature of the solvent is described in en.wikipedia.org/wiki/organic solvents. The selection of solvent is dependent on the nature of the molecule to dissolve.

The different types of solvent are mainly classified according to polarity and non-polarity. Non-polar solvents are e.g. haxane, chlorform and diethyl ether. Those mentioned are useful because the can be avaporated having boiling points between 35 and 65 facilitating removal by evaporation. Polar aprotic solvents are often used for solubilization of pharmaceutical molecules e.g. demethy sulfoxide, acetonitril. The later is of interest because it has low boiling point. Polar protic solvents are also useful particularly in combination with other solvents. Ethanol, methanol have low boiling point and acetic acid has high boiling point. Low boiling point is particularly important for the evaporation technique. The solubilisation may be done with two or more solvents. The solvents mentioned are examples and there are many more having perhaps even more desired properties for the use in the innovation for forming G3 formulations.

Examples of usable are as non-ionic, ionic i.e. cationic or anionic or Zwitter-ionic detergent such as Zwittergent or detergent based on gallic acid which is used in excess. Typical examples of suitable non-ionic detergents are N-alkanoyl-N-alkyl-glucamines, polyglycol esters and polyglycol ethers with aliphatic or aralylphatic acids and alcohols. Examples of these are alkylpolyoxyethylene ethers with the general formula $C_nH_{2n+1}(OCH_2CH_2)_xOH$, shortened to Cn Ex; alkyl-phenyl polyoxyethylene ethers containing a phenyl ring between the alkyl group and the polyoxyethylene chain, abbreviated Cn phi.Ex, Triton X-100=tertC$_8$ E$_9$6 (octylphenolether of polyethylene oxide), acylpolyoxyethylene esters: acylpolyoxyethylene sorbitane esters, abbreviated Cn sorbitane Ex, e.g. Tween 20, Tween 80, .beta.-D-alkylglucosides, e.g. .beta.-D-octylglucoside. Typical examples of suitable ionic detergents are gallic acid detergents such as e.g. cholic acid, desoxycholate, cholate and CTAB (cetyltriammonium bromide). Even conjugated detergents such as e.g. taurodeoxyoholate, glycodeoxycholate and glycocholate can be used. Other possible solubilizing agents are lysolecithin and synthetic lysophosphoilipids. Even mixtures of the above-mentioned detergents can be used. When using the dialysis method the detergents should be dialysable in not too long time.

Some surface active substances greatly facilitate matrix formation. These include the intrinsic biological membrane lipids with a polar head group and a non-polar aliphatic chain e.g. phosphatidyl choline (negatively charged) and phosphatidyl ethanolamine (positively charged).

According to one embodiment the detergent may be Triton-X-100, Tween-20, Nonidet, NP-40, deoxycholate, MEGA-10 and octylglycoside. MEGA-10 and octylglycoside can be removed by dialysis. For others other technologies can be used as mentioned e.g. the centrifugation method and column chromatography.

The soluble agent might be removed by evaporation using an organic solvent with low boiling point or by dialysis or by dialysis, chromatography, filtration or tangential flow as described in EPC-patent 0 109 942.

The water solution of saponin micelles is obtained by adding a freeze or spray dried powder as delivered from the producer. The saponin or saponin fraction is normally kept as stock solution e.g. 10 mg/ml water but not limited to that concentration and added to the water surrounding the lipid membrane at a final concentration above CMC i.e. critical micelle concentration e.g. 30 mg/liter exact figure is dependent on the *quillaja* product. The saponins are obtained as *Quillaja* Powder Extract and may be obtained from as crude *quillaja* extract (Berghausen, USA), *Quillaja* Ultra Powder QP UF 300, *Quillaja* Ultra Powder QP UF 1000 or Vax-Sap a non-fractionated *quillaja* saponn product, QHA and QHC fractions (all three from Natural Responses, Chile) or from Prodalysa, Santiago, Chile.

The invention is using a new production method wherein an artificial membrane of the sterol attached to a hydrophobic surface is produced in steps a-c). A water soluble micelle of a *quillaja* saponin product and a chemical (covalent) binding between the *quillaja* micelle and a component in the artificial membrane extracts the artificial membrane components into a water soluble complex as an innovative water soluble nanoparticulate complex i.e. G3. This complex is a held together by a chemical (covalent) linking keeping and binding the hydrophilic parts together in the water pgase and hydrophobic interactions between components remains in the center of the complex. The membrane is formed from an organic solution with a soluble agent that may be a detergent or an organic solvent.

Hydrophobic and amphipathic molecules to be incorporated into the artificial membrane, are solubilised with organic solvent or detergent together with the sterol in step b) and transferred to waterpahse by evaporation of the organic solvent. Dependent on the solvent it is removed by evaporation if the boiling point is below that of water or by dialyses or by similar techniques described for ISCOM formation. Thus, the removal of the solvent is not a part of the formation of the particle but for the formation of the artificial membrane that is not a part of the formation of the particles. Subsequent to the formation of the artificial membrane is completed there is water surrounding the artificial membrane. Into this water phase *quillaja* micelles suspended (dissolved) in water are added and the artificial membrane is extracted in the water phase and reorganization of the *quillaja* micelle to the new G3-formualtion. The composition can readily be adjusted to completely dissolve the artificial membrane into a particulate suspension in water. The composition differs from a micelle from the construction point of view that a covalent linking is involved thus an innovative particle is formed.

In steps f) and g) the water soluble micelle form of the *quillaja* product is allowed to interact to get the final product into a water phase. The first interaction in this step is a covalent binding between the *quillaja* micelle and the sterol in the artificial membrane and the second interaction is between *quillaja* triterpenoid skeleton and the sterol. Under suitable proportions all components in the artificial membrane are incorporated into water soluble *quillaja* micelle forming a new nanoparticle that will vary in size from 17 nm up to 40 nm. A larger size is obtained if lipids e.g. a phospholipid are present in the artificial membrane. The examples 2, 4, 9, 14, 15 and 16 demonstrate that various kinds of lipophilic molecules have been incorporated according the invention including DT, busulfan, roscovitine, vivolux 40 and vitamine D3.

Iscom matrix may be produced with the new method by adding at least one phospholipide to the suspension comprising sterol in step b).

The phospholipide may be chosen from derivatives of glycerol phosphates such as derivatives of phosphatidic acids i.e. lecithin, cephalin, inositol phosphatides, spingosine derivatives with 14, 15, 16, 17, 18, 19 and 20 carbon atoms, phosphatidylethanolamine, phophatidylserine, phosphatidyl choline.

Hydrphobic components may incorporated in step b) i.e. in the artificial membrane that includes also lipids, sterols.

In step d) the saponin in the water soluble form i.e. micelle form is added to the water phase covering the artificial membrane The invented nanoparticle replaces the ISCOM matrix because it simpler and more economical to produce because the nanoparticle according to the invention is based on two components i.e. a *quillaja* saponin, cholesterol in contrast to the ISCOM particle formation includes three components i.e. a *quillaja* saponin, cholesterol and the third component a phospholipid e.g. phosphatidyl choline. The *quillaja* component(s) need not to be solubilized with detergent or with an organic solvent. The new production technique according to the invention is robust and the sensitive balance is overcome. Thus, the the new method is more suitable than ISCOM matrix technologies for integration of a fourth, fifth or more i.e. other hydrophobic or amphipathic molecules since methods so far developed allow the strong tendency of such compounds to spontaneously form stable complexes (self assembly) in water e.g. micelles and therefore not being integrated into the ISCOM atrix formulation e.g. by hydrophobic interaction. Thus, the ISCOM matrix technology has shortcomings to be developed as a general delivery system, but the invention does not have such shortcomings.

All publication mentioned herein are hereby incorporated as reference. The invention will now be described by the following non-limiting examples.

EXAMPLES

Materials and Methods

Chemicals and Compounds

Cholesterol (C8667), phosphatidylcholine (PC, P-5763) and chloroform (288306) were all purchased from Sigma-Aldrich Sweden AB, Stockholm, Sweden. Fraction A (QHA) and Fraction C (QHC) of *Quaillaja saponin* are all purchased from ISCONOVA AB, Uppsala, Sweden. Diterpenoid (DT) i.e. *Stevia* was obtained from Prodalysa Ltda., Chile. Vitamin D3 was commercially obtained from Miva Nutri-molecular Research Limited, Shanghai, China.

Cell Lines

The human macrophage (Mφ) cell line U937 (which is often used as a model cell line in biological and cancer research) and the human Acute Myeloid Leukemia (AML) cell lines HL-60 were grown in culture medium RPMI-1640. The human prostate adenocarcinoma, PC-3, cultured in a 50/50 mixture of HAM's F-12K and RPMI-1640. All the cells were kindly supplied by the division of clinical pharmacology, Uppsala University. All media were supplemented with 10% heat-inactivated fetal calf serum (FCS), 2 mM glutamine, 100 μg/ml streptomycin and 100 IE/ml penicillin (all from Sigma Aldrich Co, St Louis, Mo., USA). All cell lines were incubated at 37° C. in humidified air containing 5% $CO_2$.

Human Dendritic Cells (DCs)

Immature human DCs were purchased from 3H Biomedical, Uppsala, Sweden.

In Vitro Assay Procedure

Cells in 96-well micro-titer plates at a cell density of 5,000-20,000 cells/well were exposed to serial diluted G3, KGI and *Quillaja saponin* products containing the same amounts of QHC at 37 C in humidified atmosphere containing 5% CO2 for 72 hours. For U937 cells, one set of, the cells were used directly for the fluorometric microculture cytotoxicity assay (FMCA) to measure cell killing effect of the formulations. For the other set of the cells, the supernatant was collected 150 μl/well for cytokine IL-8 determination.

Measurement of Cancer Cell Killing Effect

The FMCA method is based on measurement of fluorescence generated from hydrolysis of fluorescein diacetate (FDA) to fluorescein by cells with intact plasma membranes. After above mentioned incubation for 3 days, the medium was removed by aspiration. After one wash with PBS, 100 μl/well of FDA dissolved in a physiological buffer (10 μg/ml) was added. The plates were incubated for 45 minutes and the generated fluorescence from each well was measured in a 96-well scanning fluorometer. The fluorescence is proportional to the number of intact cells in the well. Quality criteria for a successful analysis included a fluorescence signal in the control wells of more than five times of the mean blank value, a mean co-efficient of variation (CV) in the control wells of less than 30%.

Cytokine IL-8 Determination for U937 Cells Stimulated with G3 Formulations

ELISA for the detection of human IL-8 was carried out according to the manufacturer's instruction (Human IL-8 ELISA, catalog No. S8000C, R&D system, Minneapolis, Minn. 55413, USA). Briefly, 50 μl reconstituted standards of human IL-8 and the supernatants were added to each well in triplicate wells and mixed well by gently tapping the plates several times. The plates were then covered with adhesive plate covers and incubated for one hour at room temperature (RT, 20-25° C.). After the incubation, the plates were washed 3 times with Wash Buffer and 50 μl/well of the Biotinylated Antibody Reagent (anti-human IL-8) was added. The plates were covered again with adhesive plate covers and incubated for one hour at RT. After being washed 3 times with Wash Buffer, 100 μl/well of Streptavidin-HRP Solution was applied. The plates were covered with the adhesive plate covers again and incubated for 30 minutes at RT. The contents in the plates were discarded and the plates were washed 3 times with Wash Buffer. 100 μl of TMB Substrate Solution was dispended into each well. The enzymatic color reaction was allowed to develop at RT in the dark for 30 minutes. The reaction was stopped by adding 100 μl/well of Stop Solution. The absorbance was read on an ELISA plate reader at 450 nm and 550 nm. Subtract 550 nm from 450 nm values to correct for optical imperfections in the microplates. The standard curve was then generated and used to calculate the amount of human IL-8 in the unknown samples. The standard curve was created by plotting the average absorbance obtained for each standard concentration on the vertical (Y) axis vs. the corresponding concentration (pg/ml) on the horizontal (X) axis.

Cytokine IL-12 Gene Expression of Human Monocytes Stimulated by G3 Formulation

The cytokine IL-12 gene expression of treated DCs by G3, DT, G3 with DT incorporated were compared with the cell control by gene arrays. Briefly, normal human monocytes were exposed to 10 μg/ml of G3, 100 μg/ml of DT and the combination of these two in the same particles with the same concentrations for 6 hours, then RNA was isolated according to the manufactures manual (QIAGEN RNeasy Minikit). RNA expression analysis was done at "Uppsala Array Platform, Clinical Chemistry and Pharmacology, Uppsala University Hospital Uppsala-Sweden" by converting the RNA samples to labeled cDNA via reverse transcription and comparing the quantitative data from the various samples with untreated cells (Ambion WT Expression Kit).

Thymidine Kinase (TK) Activity

The TK activity was determined with a kit obtained from Biovica (Uppsala, Sweden). Briefly, after exposing to KGI or G3 formulations at various time points, 100 μl cell suspension at a concentration of $0.1\text{-}1\times10^6$ cells/ml was transferred to Eppendorf tubes and centrifuged at 200 g for 10 minutes. The cell pellet was re-suspended in 100 μl cold PBS and freeze/thawed 2-3 times. After centrifugation at maximum speed for five minutes, then the cells were collected. The inter-cellular TK activity was measured according to the manufacturer's protocol.

Detection of Vitamin D3

Samples with cholecalciferol (vitamin D3) incorporated in G3 particles were analysed at a University Hospital Laboratory on a Liaison automatic instrument. Although the assay (DiaSorin Liaison) is designed to measure 25-HO-D3 it has about one percent cross-reactivity with non-hydroxylated vitamin D3.

Influenza Virus Strains and Vaccine

The human influenza virus A/California/07/2009 (H1N1), A Perth/16/2009(H3N2) and B/Brisbane/60/2008(B) as a non-adjuvanted vaccine was used as antigen in the preparation of the vaccines, the serological tests and in the re-stimulation of lymphocytes. The virus was cultured on VERO cells and split with deoxycolate. It was kindly supplied by the manufacturer. After harvest, the viruses were purified, inactivated, split and re-suspended at a concentration of 30 μg protein/ml. The dose contained 1 μg virus antigen and various amount of adjuvant as indicated in FIG. 1.

Vaccination

C56Bl6 mice hosted at the animal facility, University Hospital, Karolinska Institute, Stockholm, were immunized subcutaneously in the neck twice. For details, see example 12.

Haemagglutination (HA) Test

Chicken erythrocytes (RBCs) collected in citrate solution were washed 3 times using 0.01M phosphate buffered saline (PBS) pH 7.2 and re-suspended at a concentration of 0.5% in PBS containing 0.05% bovine serum albumin (BSA). The HA test was performed in U-type microplates at 4° C. for 1 hour.

Haemagglutination inhibition (HI) test

Serum samples were incubated at rum temperature (RT°) together with a 30% suspension of chicken RBCs for 1 hour (h). After absorption, the mixtures were centrifuged at 500×g for 10 min and the supernatants collected. The final serum dilution was 1:5. The HI test was carried out using V-type microplates and 16 HA-units/50 μl. Serum samples, 25 μl were 2 folds diluted using an equal amount of PBS-BSA. The diluted sera were incubated at RT° for 1 h together with 25 μl of virus suspension after which the mixtures were incubated at 4° C. for 1 h. The highest serum dilution inhibiting 100% the Haemagglutination was considered as the antibody titer for the sample.

Preparation of Lymphocytes

The spleen-lymphocytes (splenocytes) were obtained as aseptically as possible. Immunized and non-immunized mice were bled and sacrificed by cervical dislocation at 3 weeks post revaccination. Spleens were removed and thereafter carefully teased, passed through a sterile stainless steel mesh and flushed with EMEM with Tricine using a pipette. The cells were washed twice using EMEM with Tricine means centrifugation at 500×g with. Then, the pellets were re-suspended in F-DMEM medium supplemented with 1% fetal calf serum (FCS), 10 μg gentamicin/ml, 2 mMl L-glutamine, 3.81 g Hepes/L and $5\times10^{-5}$ M (3-mercaptoethanol (culture medium). The cells viability was assayed by Trypan blue dye exclusion test.

Enzyme-Linked Immunespot Assay (ELISPOT)

The enumeration of cytokine secreting splenocytes was carried out using commercial ELISPOT-kits for INF-γ, IL-2 or IL-4. The kits were purchased from Mabtech, Stockholm, Sweden. The ELISPOT plates were used following the instructions recommended by Mabtech.

For each cytokine, splenocytes at a concentration of $2\times10^5$ per 100 μl culture medium were pipette into 8 different wells. Four replicates received 50 μl culture medium containing 4.5 μg haemagglutinin of influenza virus antigen. The resting four wells received 1000 of culture medium only. Plates were incubated at 37° C. in humidified boxes for 18 h after which the cells were discarded and the wells washed. Spots were developed following the procedure described by Mabtech. In short, plates were incubated for 2 h at RT° with 100 μl biotinylated monoclonal antibodies (MoAb) anti IFN-γ, IL-2 or IL-4. Then, the plates were carefully rinsed and thereafter incubated for 1 h at RT° with HRPO conjugated Strepavidin. After another wash cycle, the plates were incubated with the substrate at RT° for approximately 15 min or until distinct spot emerged. Washing the plates with tap water stopped the reactions. Finally, the plates were allowed to dry and thereafter the number of spots was counted using an ELISPOT counter.

Data Analysis and Statistics.

Dose-response data were analyzed using calculated SI values and the software program GraphPadPrism4 (GraphPad Software Inc., San Diego, Calif., USA). Data are presented as mean values±SE. Statistical inferences between several means were performed by one-way ANOVA with Tukey's multiple comparison post test of group means and for comparison of two means, by Student's t-test, in GraphPadPrism.

Part I. Formulation and Characterization

Example 1

In this example, the formulation of the G3 nanoparticles is described. In experimental set up step 2, A and B, (see below) the influence of the proportions of cholesterol vs QHC fraction (from ISCONOVA AB, Uppsala, Sweden, see WO2008/063129) of *Quillaja saponin* has been explored. In C the effect of adding a phospholipid is explored with regard to particle formulation.

Experimental Set-Up

In step 1 an artificial cholesterol membrane is formed requiring a solubilisation in detergent or organic solvent. In this experiment we have used chloroform (288306, Sigma-Aldrich Sweden AB, Stockholm, Sweden) as the solvent for cholesterol (C8667, Sigma-Aldrich Sweden AB, Stockholm, Sweden) to generate a stock solution of 100 mg/ml. In an Eppendorf tube, 2 µl of cholesterol from the stock solution diluted in 50 µl chloroform was added, subsequently ½ ml of water was layered on the top of the cholesterol solution. The chloroform was evaporated by a stream of air created with a syringe with a needle. A visible layer of cholesterol was seen on the wall of the tube.

In step 2

The ½ ml of water was replaced by 1 ml of fresh water and 10 µl of the QHC stock solution (100 mg/ml in water) was added to the water, followed by incubation over night at 37° C. The membrane disappeared from the wall and a clear water solution is seen.

A. Two µl of cholesterol stock solution and processed as described step 1 and 10 µl of the QHC in step 2 were used to generate this G3 formulation, which gave a molar ratio of 1:1

B. Another molar ratio was also used i.e. 2 mol of cholesterol vs. 1 mol of QHC. Otherwise, the experiment was the same as for A C. A ratio of 1 mol cholesterol and 1 mol phosphatidylcholine (P-5763 is from Sigma-Aldrich Sweden AB, Stockholm, Sweden) were used to form the membrane in step 1. In step 2, two mol of QHC was used.

Results

A. After evaporation, a 17 nm particle having a uniform size was achieved characterized by electron microscopy (EM) see FIG. 1A and by gradient centrifugation. The G3 suspension is visualized as a clear solution.

B. After evaporation, particles of a slightly wider size range were observed in EM with a medium diameter of about 17 nm (not shown), i.e. 17 nm particles were also created within the range of 2 mol of cholesterol and 1 mol of *Quillaja saponin*.

C. The product had morphology like that of ISCOM particles with a diameter of about 40 nm (FIG. 1B) Thus, the morphology is completely different with the inclusion of phosphatidylecholine from that of the nanoparticles according to the G3 invention without the phophatidylecholine. It can also be concluded that the nanoparticles according to the invention is an excellent basis for integration of phopholipids including phosphatidylecholine being essential for ISCOM formulation as claimed by Lövgren & Morein[1].

Conclusion and Discussion

With the molar ratio of 1 cholesterol to 1 *Quillaja*, small (17 nm) nanoparticle is formed. The higher ratio of cholesterol i.e. molar ratio of 2 cholesterol vs 1 *Quillaja* or more, then larger particles appear. To note, by inclusion of other lipophilic components in step 1, the size of the particle will vary, i.e. the loading of the particle influences the size. In this case, the range of size was recorded between 17 and 40 nm but that is not the limitation of the range. Especially important is that in EM no aggregation of the particles was seen rather the particles were well dispersed from each other.

An essential and new concept to render lipophilic substances water soluble is this two step procedure. There are various ways of forming lipid membrane e.g. liposomes that have no solid hydrophobic support, but are in free suspension in a water phase. The second step extracts the membrane into the water phase via first into the water soluble G3 particle.

To note, the procedure for forming nanoparticles according to the invention is robust and much simpler than now used methods e.g. to make ISCOM formulations (Lövgren & Morein, see above). Above all, with the evaporation used there is hardly any loss of material used for the particle formulation i.e. *Quillaja* saponin in the referred case QHC or cholesterol and no phospholipid is required, further reducing the production costs. Interestingly, the nanoparticles according to the invention can be used as a base for forming ISCOMs.

If detergent is used for solubilisation the removal of detergent has to be done as described by Lövgren &Morein[2] e.g. by dialyses, column chromatography, ultracentrifugation or tangential flow it may be more practically to use beads (e.g. latex beads) with a hydrophobic surface. Thus, the two step procedure is an innovative robust method to formulating nanoparticles, which may vary in morphology depending on the load.

Moreover, this method that in step 1 formulates a membrane is a general method for incorporating lipophilic molecules into the water soluble G3 particle in step 2.

Example 2

This example shows that a molecule with amphipathic properties can be incorporated into the G3 particles according to technology as described in Example 1. To note G3 is naturally soluble in water as a micelle being disintegrated after administration due to dilution at the site of injection and subsequently after the transportation from the site. It has therefore low poor biovailability. Consequently a stable complex in G3 is important.

Experimental Set-Up

The experiment set-up is essentially the same as for Example 1, apart from that a hydrophobic molecule diterpenoid (DT) was also solubilized at the same time with cholesterol as described for Example 1. The DT molecule together with Quil A fraction C (QHC) and cholesterol was incorporated in the G3 particle using the same two steps procedure as in example 1 i.e. 1 µl DT (100 µg/ml in 99% ethanol as the stock solution) was solubilized in a molar ratio of 1 cholesterol:0.5 DT described for step 1 in example 1. In step 2, QHC was added in to molar ratio of 1 to 1 with cholesterol in example 1.

Results

The G3 particle with incorporated DT has the same morphology as the G3 particle without DT depicted in FIG. 1A. In step 1 a membrane was visualized on the walls of the tube that disappeared in step 2. The water solution from step 2 is clear to slightly opalescent and no sediment was detected.

Conclusion

The amphipathic molecule diterpenoid (DT) in the micelle form has been successfully disintegrated by the solvents used and in step 2 integrated into the nanoparticles according to the invention, resulting in typical G3 nanoparticles of 17 nm. Thus, the capacity to use the G3 nanoparticles according to the invention as a carrier/delivery system for an amphipathic molecules is shown. Amphipathic molecules with required configuration form micelles mostly instable after administration into individuals that often results in low bioavailabiltity. In example 4 it is shown that this G3-DT particle is biology active. Further studies will be performed during the Paris Convention priority year to further prove the immune enhancing capacity and usefulness of the nanoparticles according to the invention as delivery particles and for enhancing biological effects by interaction with cells e.g. via receptors in the cells membranes. For more information see Hu et al.[3], incorporated herein by reference. By incorporation of other molecules with complementary properties including the immune enhancing and the cancer cell killing effects will potentially be substantially broadened.

Example 3

The capacity of G3 to kill cancer cells were tested in vitro on the U937 model representing a lymphoid tumour cell.

Experimental Set-Up

G3 particles were formulated with various weight or molar ratios between cholesterol and QHC as described in Materials and Methods. The various formulations were incubated and the cancer cell killing effect was measured after staining and reading by the FMCA method as described in Materials and Methods.

Results

G3 particles formed with the ratio of 1 cholesterol vs 5 QHC according to the weight i.e. 1 cholesterol vs 1 QHC according to the molarity, as described in Ex 1 and concluded from morphology according to the EM results (see Exl and FIG. 1A.). The U937 cancer cell killing effect of G3 particle was of the same magnitude as for KGI particles (FIG. 2), indicating that the active component QHC was preserved when incorporated in the G3 formulation. KGI has previously been known to kill U937 cancer cells (PCT/SE 2007/050878).

Example 4

This example shows that the amphipathic molecule DT can be incorporated into the G3 particles according to technology as described in Examples 1 and 2.

DT is a diterpen, a stevioside produced from *Stevia rebaudiana* bertoni[10]. We have used DT because it has a number of interesting medical including immunological properties as published[11]. One problem with this compound is that it has low bioavailability in vivo as we have experienced requiring a delivery system e.g. in a nanoparticle.

The capacity of DC to induce the cancer cell U937 to produce IL-8 was done to explore immunological effect but even more importantly to demonstrate with this cytokine that DC may lead the cancer to differentiation being important to ceasing the uncontrolled cancer cell proliferation. Furthermore, the capacity of DT to induce human DC cytokines including IL-12 was tested. These tests were carried out to emphasize that DT has an important complementary immunological effect to Quil A and it is, therefore, useful to be incorporated in the G3 particles. DT was supplied by Prodalysa LTDA, Santiago, Chile. Here we used human dendritic cells (DC) prepared as described in Material and Methods.

Experimental Set-Up

The U937 cells were incubated with KGI or G3 formulations starting from 100 μg/ml followed by 5-fold dilutions for 6 steps for 48 hours at 37° C. Then the supernatant was collected and used for IL-8 detection as described in Materials and Methods For the measurement of gene expression, human DCs were incubated with BBE, KGI, *Stevia* and *Stevia* in combinations with BBE or KGI (FIG. 4A) as well as G3 with or without *Stevia* incorporated (FIG. 4B) for 6 hours. The expression of various cytokine genes from the treated DCs was carried out by mRNA array analysis as described in Materials and Mathods.

Results

G3 particles induced U937 cancer cells to produce a similar level of IL-8, which is a differentiation marker of the cancer cell, production to that induced by KGI (FIG. 3).

FIG. 4A shows that DT induced high levels of IL-12, IL1β and IL-6, higher than those induced by the ISCOM like formulations KGI and BBE The G3 particles with DT incorporated induced high level of IL-12, while the G3 formulation without DT incorporated did not induce detectable level of IL-12 (FIG. 4B).

Discussion and Conclusion

DT has complementary properties to G3. The capacity to induce the U937 cancer cells to produce IL-8 may indicate immune enhancement. More importantly, G3 standalone can differentiate and lead the cancer cell to cease proliferation like KGI as we have shown (manuscript in preparation to be supplemented). Complemetary effect to G3 alone it is shown that DT potently induces IL-12, which is important for induction of a Th1 type of response particularly for production of IFN-, which has anticancer effect for certain tumors. From immunological point of view, IL-12 is important for rejection of tumors if there are tumor antigens recognized by the immune system. IL-12 is also important for the immune defense against virus infections. It is of particular interest to record that DT is incorporated into G3 serving as a carrier/delivery particle, which increases its stability in a particle form after administration and consequently increases G3's bioavailability. To note, DT stand alone is in a micelle form in water. A micelle formation administered into the body of an individual disintegrates because the dilution at the site of administration and subsequently decreases as it is transported from the site. The G3 particle is held together by other forces and does not disintegrate e.g. after injection that has been recorded by EM studies (not published). This example emphasizes that the G3 invention serves as carrier for amphipathic molecules.

Example 5

Inhibition of thymidine kinase (TK) activity by G3 particles is an essential property to prevent uncontrolled replication of cancer cells and for the subsequent steps to steer the cell to a programmed cell death i.e. apoptosis.

To explore one mechanism of G3 particle to inhibiting the cancer cell replication was evaluated by measuring the inhibition of TK enzymatic on U937 cells. Besides using inhibition of the TK enzyme activity for showing inhibition of cancer ell replication this mode of action will be used to evaluate whether G3 particles or any other *quillaja* formulation used for anticancer treatment will be useful to treat tumour patients stand alone or in combination with other anticancer formulations. Such a test can be used in a kit to measure the sensitivity of anticancer drugs using inhibition of TK mode of action on clinical samples in the field defined as personalized medicine.

Experimental Lay-Out U937 cells were exposed to the same amounts of G3 or KGI. At various time points, the treated cells were collected and inter-cellular TK activities were measured as described in Materials and Methods.

Results

G3 particles inhibit virtually the same magnitude of inter-cellular TK activities as that by KGI (FIG. 5).

Conclusion

The inhibition of TK activity shows that the cancer cell ceases to replicate. The inhibition of TK activity on the cellular level can therefore be used to measure the sensitivity of cancer cell from the patient samples to the drug i.e. the G3 particles, paving the way to personalized medicine. To our knowledge, TK activity has been used as a non-specific test for the detection of serum TK from cancer patients or other disease indications from patients: By using it directly on cancer cells from patients is our innovation (with 100% specificity i.e. only cancer cells are used). This, together with the cancer cell killing property, makes G3 particles more feasible for clinical use by avoiding its use on non-responding patients.

Part II. G3 as an Anticancer Drug

Example 6

This example shows G3 and G3 with DT (G3-DT) kills the non-solid tumor human Acute Myeloid Leukemia (AML) cells more efficiently than the active component QHC (QHC) in G3 in a non-particulate form.

Experimental Set-Up

The nanoparticles G3 and G3DT formulated as described in Ex 1 and 2 were compared with the active component QHC form for the cancer cell killing effect. The samples were 5-fold serial diluted in 6 steps starting from 100 µg/ml, and incubated or 3 days with HL-60 AML cells f. Then the cells were stained and read by the FMCA method.

Result

G3 ($IC_{50}$=3.144 µg/ml) and G3-DT ($IC_{50}$=3.12 µg/ml) inhibited the growth of the AML cells more efficiently than QHC (IC50=8.473 µg/ml) (FIG. 6).

Conclusions and Discussions

Essentially, G3 has a stronger cancer cell killing effect compared to that of the non-particulate QHC. Incorporating DT into the G3 particles forming G3-DT enhances the cancer cell killing effect compared to either QHC or G3 without DT. DT alone has no cancer cell killing effect (not shown). The non-particulate QHC causes local reaction that is abolished by the particulate forms. The added effect of G3-DT in killing AML cancer cells would also implicate a beneficial dose reduction.

Example 7

Cytarabine is a commercially available cytostatic drug used for treatment of Acute Myeloid Leukemia (AML). This example was set up to explore the capacity of G3 to enhance the cancer cell killing effect of cytarabine.

Experimental Set-Up

Figure 7:
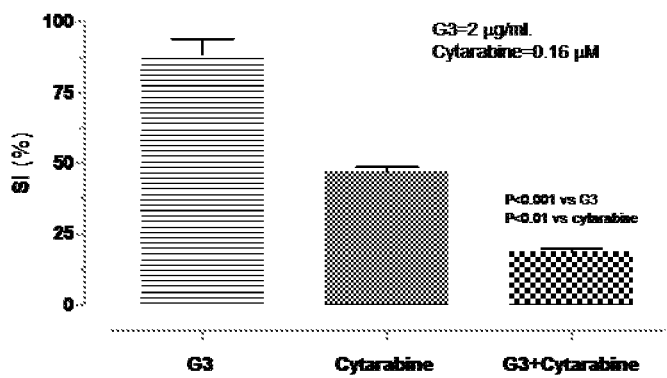

HL-60 AML cells were exposed for 3 days at pre-determined concentrations of G3 and cytarabine separately and in combination of these two as shown on FIG. 7. Then the cells were stained and read for cancer cell killing effect by the FMCA method.

Result

After incubation for 3 days, G3 or cytarabine alone killed less than 5% and 55% the cells respectively. When they were combined, the killing rate was elevated significantly ($P<0.01$) to about 75% (FIG. 7).

Conclusions and Discussions

The G3 particles significantly enhance the killing effect of cytarabine on HL-60 AML cells. Treatment with the cytostatic drug cytarabine causes side effects with discomfort for patients. Since G3 particles are virtually non-toxic, the combination treatment with G3 and cytarabine would also have prospect for increased efficacy and reduce the side effect by lowering the dose of cytarabine.

Example 8

This example demonstrates that G3 has added cancer cell killing effect on the commercial cytostatic cancer drug daunorubicin on the non-solid tumor human Acute Myeloid Leukemia (AML) cells.

Experimental Set-Up

HL-60 AML cells were exposed to a fixed concentration (1 µM) of G3 combined with increasing concentrations of daunorubicin starting from 1000 nM, and incubated for 3 days. Then the cells were stained and read by the FMCA method.

Result

Figure 8:
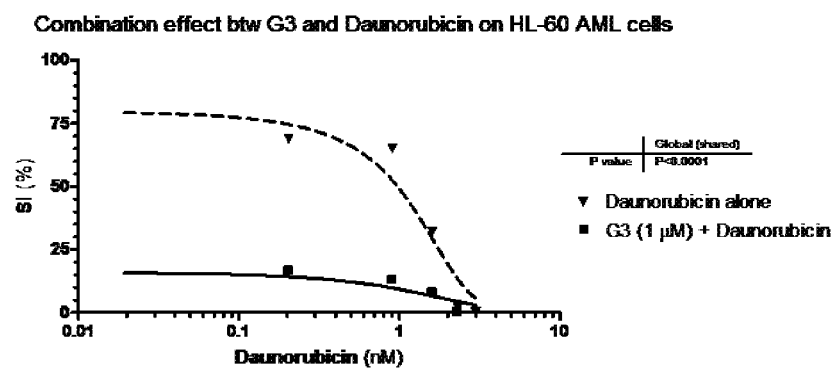

G3 enhances significantly ($P<0.0001$) the cancer cell killing effect of daunorubicin compared to daunorubicin stand alone (FIG. 8).

Conclusions and Discussions

The G3 particles enhance synergistically the killing effect of daunorubicin on HL-60 AML cells. Since G3 particles are virtually non-toxic, it is likely the dose of the cytostatic drug daunorubicin would be considerably reduced in a combination therapy with G3 implicating better treatment effect, and because of lowered side effect the treatment can be continued for longer periods in patient sensitive to daunorubicin Example 9

This example was designed to compare the effects of G3 and G3 with DT incorporated (G3DT) on solid tumors exemplified by human prostate cancer cells PC-3.

Experimental Set-Up

G3 and G3DT was compared with non-particulate QHC. The samples were 5-fold serially diluted in 6 steps starting from the concentration of 100 µg/ml, and incubated with PC-3 prostate cancer cells for 3 days. Then the cells were stained and read by the FMCA method.

Result

Figure 9:
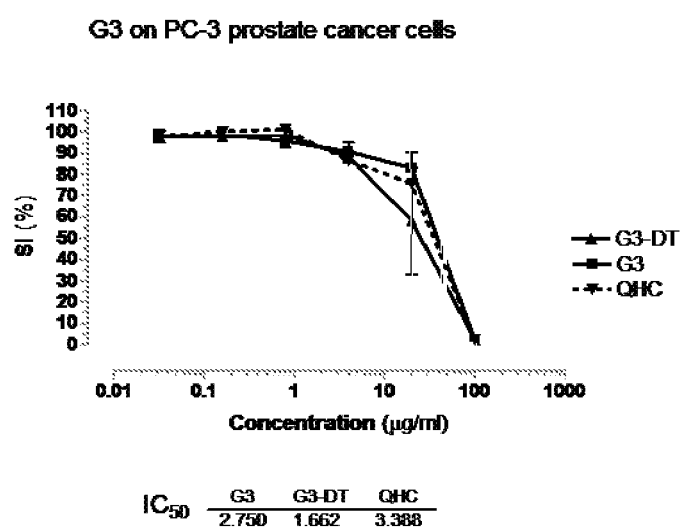

The G3 particles ($IC_{50}$=2.75 µg/ml), and the G3-DT ($IC_{50}$=1.662 µg/ml) incorporated inhibited the growth of the prostate cancer cells more potently than the same active component QHC alone ($IC_{50}$=3.388 µg/ml) (FIG. 9)

Conclusions and Discussions

Essentially, G3 in this example had a similar killing effect on the PC-3 prostate cancer cells as that of QHC. By incorporation of DT into the particle i.e. G3-DT, the cancer cell killing effect of G3 is, as with AML cells, enhanced. It is known that DT alone has no cancer cell killing effect. Its added effect here in killing PC-3 cancer cells implicates enhancement of the G3 effect and also reduction of the side effects if any. To note the QHC in non-particulate form is comparatively efficient in vitro but in vivo QHC remains at the site of injection resulting in low bioavailability and local side effects.

Example 10

This example demonstrates that the combination effect between G3 and a commercial drug docetaxel on solid tumors exemplified by PC-3 prostate cancer cells.

Experimental Set-Up

PC-3 cells were exposed for 3 days at pre-determined concentrations of G3 and docetaxel separately and in combination as shown on the graph. Then the cells were stained and read by the FMCA method.

Result

Figure 10:
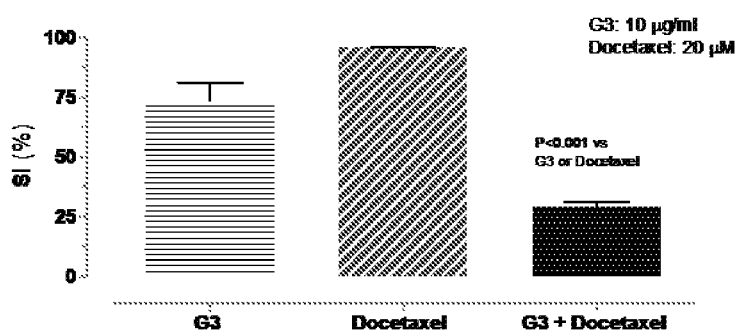

The cancer cell killing effect of G3 or docetaxel alone killed slightly more than 35% and 2% the cells respectively. When these two drugs were combined, the killing rate was significantly elevated (P<0.01) to about 75%. (FIG. 10).

Conclusions and Discussions

The G3 particles significantly enhance the cancer cell killing effect of the cytostatic docetaxel on the prostate PC-3 cancer cells implicating increased efficacy and reduced dosing of the cytostatic drug with reduced side effect in view of the fact that G3 particles are virtually non-toxic.

Example 11

This example was designed to explore combination effect between G3 and a recent and under patent covered cytostatic commercial drug cabazitaxel on the solid tumor human prostate cancer PC-3 cells.

Experimental Set-Up

PC-3 prostate cancer cells were exposed to a fixed concentration (1 μM) of G3 combined with increasing concentrations of cabazitaxel starting from 100 μM, and incubated for 3 days. Then the cells were stained and read by the FMCA method.

Result

Figure 11:
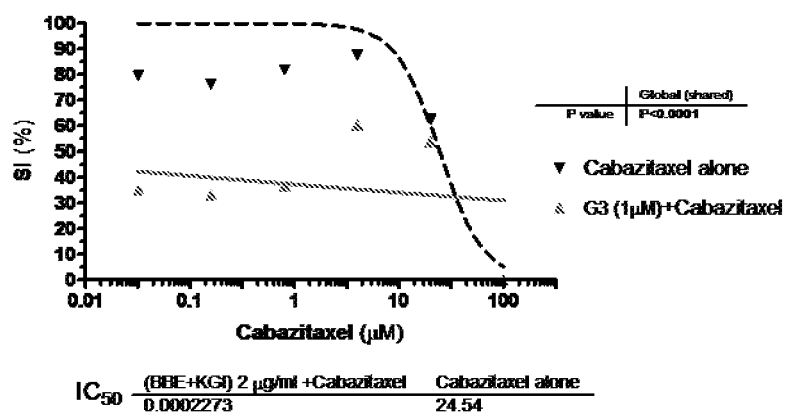

Cabazitaxel alone killed the PC-3 cancer cells at, G3 at an $IC_{50}=25.54$ μM. Cabazitaxel combined with G3 the cancer cell killing effect ($IC_{50}=0.00023$ μM) was significantly (P<0001) enhanced (FIG. 11).

Conclusions and Discussions

The G3 particles significantly and synergistically enhance the killing effect of cabazitaxel on PC-3 prostate cancer cells implicating prospects for better efficacy, reduced side effect and possibility for prolonged treatment in view of the fact that G3 particles are virtually non-toxic,

Example 12

This example was designed to explore the capacity of G3 particles formulated with another important *Quillaja* saponin fraction QHA in killing solid tumours exemplified here with ACHN kidney cancer cell line since it was observed before that Duecom particles formulated with this fraction had a stronger killing capacity than Duecom particles formulated with Fraction C (QHC).

Experimental Lay-Out

G3 formulated with QHA and QHC were diluted 5-folds, 6 steps from 100 μg/ml down to 0.032 μg/ml and incubated with ACHN renal carcinoma cells at 37° C. for 3 days. The cell survival was determined by the FMCA method.

Result

Figure 12:
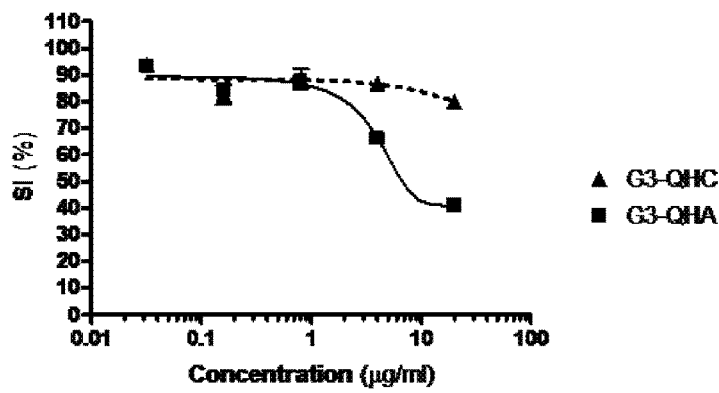

G3 formulated with QHA kills significantly (P<0.01) more ACHN kidney cancer cells than that of G3 formulated with QHC (FIG. 12).

Conclusions and Discussions

This result is virtually identical to the previous observation with Duecom particles formulated with QHA and QHC i.e. that formulations with QHC is selectively killing more non-solid tumour cells while formulations with QHA is preferably killing more solid than non-solid tumours. This tumour type specific killing property with G3 formulations could be harnessed as for Duecom particles to avoid killing normal cells in another category.

Part III. G3 as Adjuvant

Example 13

Animal trial of G3 particle as an adjuvant against whole virus

The adjuvant effect of G3 in comparison to ISCOMs was evaluated in an animal trial on C57BL/6 mice. The disintegrated and inactivated influenza virus was used as the model antigen in the experiment.

Experimental Lay-Out

Six mice per group, immunized twice 4 weeks apart, blood samples were taken at 3 weeks after the first immunization and 4 weeks after the second immunization (see the graphic description on next page). At the necropsy i.e. 4 week after the second immunization, spleen cells were analyzed for cytokine production as described in materials and methods. To facilitate the understanding, grouping of the animals is shown in FIG. 13A.

Result

The G3 and ISCOM induced in dose dependent manner detectable levels of HI antibody after the $1^{st}$ immunization. After the $2^{nd}$ immunization, the level of HI antibody increased considerably (a clear boost effect) also in a dose dependent manner for the G3 adjuvanted formulations. The ISCOM, G3 and G3 with DT incorporated adjuvanted formulations induced considerably higher levels of HI antibody than the non-adjuvanted commercial vaccine, i.e. similar or higher levels of HI responses were recorded between animals immunized with G3 and ISCOM formulations at two time points after the $1^{st}$ (FIG. 13A) and the $2^{nd}$ (FIG. 13B) immunizations.

Figure 13C:
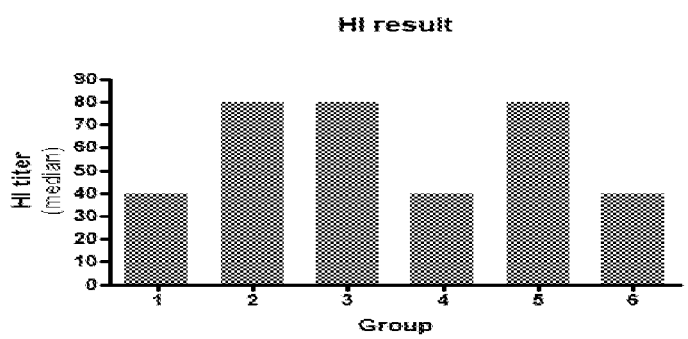
Figure 13D:
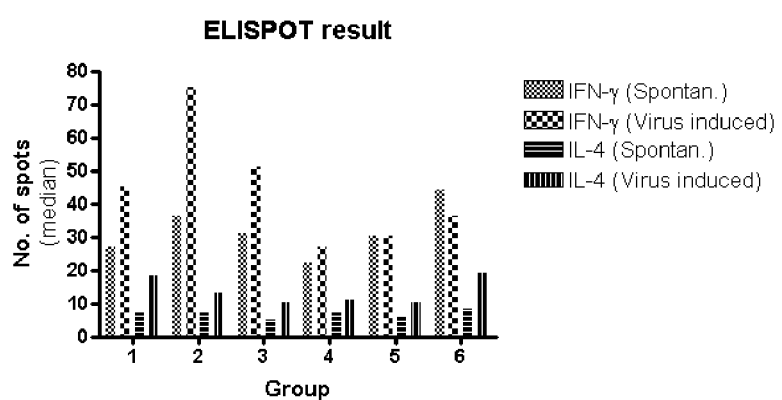

Similar or even higher levels of IFN-γ and IL-4 responses were detected in spleen cells after in vitro re-stimulation with the split virus between animals immunized with G3 and ISCOM formulations at the necropsy, 4 weeks after the $2^{nd}$ immunization (FIG. 13C).

Conclusion

Both antibody-mediated and cell-mediated immunities induced by G3 and ISCOM formulations are qualitatively and qualitatively the same, i.e. G3 formulations i.e. G3 and G3DT can replace the ISCOM as adjuvant.

Part IV. G3 as a Drug Delivery System

Example 14

VLX40 was considered to be a promising drug for treating cancer. The research to market ceased because VLX40 could not be formulated to be suitable for administration to animals in preclinical tests and consequently not for subsequent tests in patients. The reason was that VLX40 could not be rendered soluble in water, which is necessary to be taken up by the body. This experiment was designed to find out if the G3 technology could solve the problem and make VLX40 water soluble.

Experimental Set-Up

VLX 40 was first dissolved in an organic solvent DMSO to yield a concentration of 20 mM (5.8664 mg/ml, the highest concentration recommended) and designated as the stock solution.

VLX40 at a concentration of 100 □g/ml was used as a control for VLX40 in water i.e. as a virtually non-water soluble formulation.

8.5 µl of the VLX40 stock solution was mixed with 50 µl chloroform in an Ependorf tub containing 500 µl water to form an artificial lipid membrane (see Example 1). In the second step, the 10 µl Quil A (100 mg/ml in water as the stock solution) was added and incubated overnight at 37° C. This is the G3-VLX40 formulation, essentially formed in the same way as described in Example 1.

The VLX40-DMSO control (2) and the G3-VLX40 suspension/solution (3) were collected and tested on U937-GTB cells after being serially diluted from the same concentration as above, and IC50s were calculated from the regression curves.

Results

The stock solution (1) added to water gave rise to a visible sediment or precipitate i.e. as expected from previous experiments. Thus, VLX40 could not be dissolved in water from the control tube (2). The formulation of G3-VLX40 particles (3) was confirmed by electron microscopy of the clear solution/suspension. There was no precipitate or only very scanty precipitate from the tube containing the G3-VLX40 formulation.

The various formulations were tested for function i.e. in bioassay for the cancer cell killing effect of U937 cells (see Materials and Methods). The water phase of the VLX40/DMSO (2) had low anticancer effect (expressed as IC 50), meaning that just a very small fraction of VLX 40/DMSO mixture is dissolved in water (FIG. 14 A).

Figure 14A:
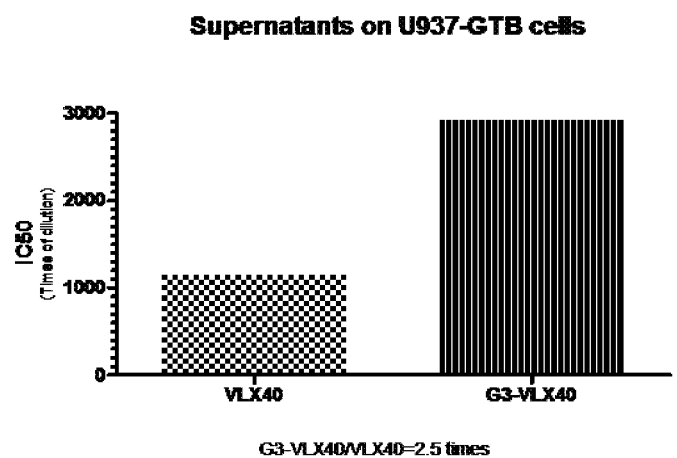

In contrast, the water phase of the G3 VLX-40 particle formulation (3) had high anticancer cell activity as shown in FIG. 14A.

Figure 14B:
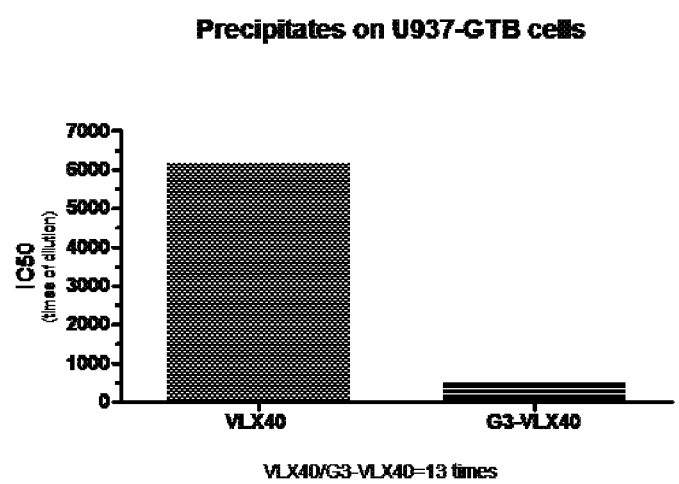

The sedimented non-soluble part was also tested in vitro for the cancer cell killing effect. High cancer cell killing effect was recorded with VLX 40/DMSO (2) in the water-insoluble precipitate, the scanty water-insoluble precipitate of G3-VLX 40-formulation had a low cancer cell killing effect (FIG. 14B).

These experiment has been repeated 3 times.

Conclusion and Discussion

About 50-100 micrograms VLX 40 was dissolved with 2 mg G3 measured as the *Quillaja* component in a volume of 1 ml of water. It should be noted that the concentration of G3 particles can be increased by increasing the concentration of the G3 particles, for example 10 mg/ml of the G3 formulation can be in a clear solution. We can also change the composition of the G3 particles to facilitate the incorporation of larger amount VLX 40. This example clearly demonstrates that the G3 particle is filling an unsolved demand to facilitate formulation of drugs for clinical use that without the G3 technology could not reach the patient because the drugs could not be made water soluble with the existing technologies.

Example 15

This example demonstrates that G3 particle, as a drug delivery system, can incorporate readily another two non-water soluble anticancer drugs busulfan and roscovitine, making them water soluble.

Experimental Set-Up

Two µl busulfan (50 mg/ml in DMSO) or 10 roscovitine (100 mg/ml in chloroform) together with 2 µl cholesterol (100 mg/ml in chloroform) were used to form the lipid membrane with busulfan or rocovitine respectively, using the way method as described for step 1 in Example 1. Then 10 µl QHC (100 mg/ml in water) was added as for step 2 in Example 1 to give a molar ratio of QHC:cholesterol:busulfan/roscovitine=1:1:0.5.

Result

For both compounds i.e. busulfan and roscovitine, clear solutions were visualized i.e. sediment or cloudiness in the water phase caused by the insoluble drugs were eliminated by incorporating them into the water soluble G3 particles.

Discussion

This example, similar to example 13, shows once again that the capacity of G3 as a general platform for making non-water soluble lipiphilic drugs/molecules water soluble by incorporating them into the G3 particles. Considering that about 40% of the anticancer drug candidates are not water soluble, therefore, cannot be further developed into commercial products, our invention can drastically improve the situation.

Example 16

In this example, we have explored whether a lipophilic vitamin i.e. vitamin D3 can be integrated into the G3 nanoparticle in order to make it water soluble. It was dissolved in chloroform and incorporated into the G3 particle as described in example 1 and for more details see Materials and Methods.

Experimental Set-Up

G3 particles were formed using 50% cholesterol and 50% vitamin D3 to form the lipid membrane. Quil A was added into the water phase to generate the G3 particles (for details, please refer to Example 1). 100% Cholesterol and 100% Vitamin D3 in water were used as the controls. Samples with vitamin D3 incorporated in G3 particles were analysed at the Uppsala University Hospital Laboratory on a DiaSorin Liaison automatic instrument.

Result

The water phase recovered in step 2 was a clear solution and no sediment could be detected. More vitamin D3 was detected in the G3-vitamin D3 formulation based on non-fractionated *quillaja* (950 nmol/L) than in the *quillaja* QHC fraction formulation i.e. 55 nmol/L. In a dilution experiment the concentration of vitamin D3 was linear in the read out showing that there was a homogenous suspension of particles i.e. no aggregation being in agreement with other G3 particles as seen in FIG. 1. In comparison, only trace amount of Vitamin D3 was detected in the vitamin D3 control and no vitamin D3 was present in the cholesterol control.

CONCLUSION AND DISCUSSION

Vitamin D3 is an essential vitamin that is poorly taken up by the body in the lipid form by oral or parenteral routes. Thus, a water soluble form will facilitate its uptake by those routes. We show in this experiment that vitamin D3 is incorporated into the G3 nanoparticle with the non-fractionated as well QHC fraction of *quillaja* saponin. Importantly, the linear read out of the dilution experiment shows a homogenous dispergation of the particles that has been revealed by electrone microscopy for G3 particles in general (see FIG. 1) For food the non-fractionated *quillaja* saponin is well accepted and used e.g. in beverages including bear and also other types of food. Therefore, the more economical alternative for the formulation of G3 for delivery of this vitamin is a non-fractionated *quillaja* as base for the G3 formulation. In this experiment more D3 was incorporated into the G3 with non-fractionated *quillaja* saponin than in the G3 particle with the QHC saponin fraction.

REFERENCES

[1] Kefei Hu, Saideh Berenjian, Rolf Larsson, Joachim Gullbo, Peter Nygren, Tanja Lövgren, Bror Morein Nanoparticulate *Quillaja saponin* induces apoptosis in human leukemia cell lines with a high therapeutic index. *International Journal of Nanomedicine*, January 2010 Volume 2010:5 Pages 51-62

[2] Lövgren & Morein (2000) ISCOM Technology in Methods in Molecular Medicine, Vol 42: 239-258, Vaccine adjuvants: Preparation Methods and Research Protocols, Edited by D.T.O O'Hagen, Humana Press, Inc., Titawa, N.J.

[3] Morein B, Hu K, Lövgren K and D'Hondt E. New ISCOMs meet unsettled vaccine demands in Vaccine Adjuvants and Delivery Systems, Ed. by Singh M. A John Wiley & Sons, Inc., Publication, Hoboken, N.J. 2007, p 191-222.

[4] Lycke, N. From toxin to adjuvant: The rational design of a vaccine adjuvant vector, CTA1-DD/ISCOM. Cell Microbiol 2004, 6(1), 23-32, and by Mowat et al. (2001)

[5] Mowat, A. M., Donachie, A. M., Jagewalll, S., Schon, K., Lowenadler, B., Dalsgaard, K., et al. CTA1-DD-immune stimulating complex: a novel, rationally designed combined mucosal vaccine adjuvant effective with nanogram doses of antigen. J. Immunol 2001, 167(6), 3398-3405

[6] Blair A H, Ghose T I. Linkage of cytotoxic agents to immunoglobulins. *J Immunol Methods.* 1983 Apr. 29; 59(2):129-43.

[7] Ghose T I, Blair A H, Kulkarni P N. Preparation of antibody-linked cytotoxic agents. *Methods Enzymol.* 1983; 93:280-333.

[8] Davis M T, Preston J F. A simple modified carbodiimide method for conjugation of small-molecular-weight compounds to immunoglobulin G with minimal protein cross-linking. *Anal Biochem.* 1981 Sep. 15; 116(2):402-7.

[9] Eliasson D G, El Bakkouri K, Schön K, Ramne A, Festjens E, Löwenadler B, Fiers W, Saelens X, Lycke N. CTA1-M2e-DD: a novel mucosal adjuvant targeted influenza vaccine. *Vaccine.* 2008 Feb. 26; 26(9):1243-52. Epub 2008 Jan. 10.

[10] A. Esmat Abou-Arab, Azza Abou-Arab and M. Ferial Abu-Salem, Physico-chemical assessment of natural sweeteners steviosides produced from *Stevia rebaudiana* bertoni, African Journal of Food Science, Vol4 (5) pp 269-281, May 2010.

[11] Chaiwat Boonkaewwant, Chaivat Toskulkao, and Molvibha Vongsakul. Anti-Inflammatory and Immunomodulatory Activities of Stevioside and Its Metabolite Steviol on THP-1 Cells, J. Agric. Food Chem. 2006, 54, 785789 7)

[13] Kersten, G. F. A., Spiekstra, A., Beuvery, E. C. and Cromelin D. J. A. (1991) On the structure of immune-stimulating saponin lipid complexes (ISCOMs). BBA 1062, 165-171.

The invention claimed is:

1. A method for producing phospholipid-free nanoparticles comprising the steps
   a) providing a hydrophobic surface or a suspension of liposomes;
   b) bringing the hydrophobic surface or the suspension of liposomes into contact with a solution of sterol dissolved as monomers in an organic solvent or detergent;
   c) removing the solvent or detergent forming a sterol membrane on the surface;
   d) providing a water solution of *quillaja* saponin micelles; and
   e) adding the water solution comprising the saponin micelles to the sterol membrane, whereby a complex is formed between the saponins and the sterols and is suspended in the water solution.

2. A method for production of Iscom matrix according to claim 1, wherein at least one phospholipid is added to the suspension comprising sterol in step b).

3. The method according to claim 1, wherein said sterol is cholesterol.

4. The method according to claim 1, wherein the organic solvent is ethanol and/or chloroform.

5. The method according to claim 1, wherein the organic solvent or detergent is removed by evaporation.

6. The method according to claim 1, wherein said solvent or detergent is removed by dialysis, chromatography, filtration or tangential flow.

7. The method according to claim 3, wherein the ratio between cholesterol and *quillaja* saponin is from 1:10 to 10:1.

8. The method according to claim 3, wherein the ratio between cholesterol and *quillaja* saponin is from 1:2 to 2:1.

* * * * *